US011306131B2

(12) United States Patent
Robbins et al.

(10) Patent No.: US 11,306,131 B2
(45) Date of Patent: Apr. 19, 2022

(54) T CELL RECEPTORS RECOGNIZING HLA-A1- OR HLA-CW7-RESTRICTED MAGE

(71) Applicant: The United States of America, as represented by the Secretary, Department of Health and Human Services, Bethesda, MD (US)

(72) Inventors: Paul F. Robbins, Chevy Chase, MD (US); Steven A. Rosenberg, Potomac, MD (US); Shiqui Zhu, Potomac, MD (US); Steven A. Feldman, Redwood City, CA (US); Richard A. Morgan, Columbia, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 491 days.

(21) Appl. No.: 16/144,226

(22) Filed: Sep. 27, 2018

(65) Prior Publication Data

US 2019/0016777 A1  Jan. 17, 2019

Related U.S. Application Data

(62) Division of application No. 14/344,354, filed as application No. PCT/US2012/054623 on Sep. 11, 2012, now abandoned.

(60) Provisional application No. 61/535,086, filed on Sep. 15, 2011.

(51) Int. Cl.
*C07K 14/725* (2006.01)
*C07K 14/705* (2006.01)
*G01N 33/574* (2006.01)
*C07K 16/28* (2006.01)
*A61K 39/00* (2006.01)

(52) U.S. Cl.
CPC .... *C07K 14/70503* (2013.01); *C07K 14/7051* (2013.01); *C07K 16/2803* (2013.01); *G01N 33/574* (2013.01); *G01N 33/57407* (2013.01); *A61K 2039/5158* (2013.01); *C07K 2317/73* (2013.01); *C07K 2318/20* (2013.01)

(58) Field of Classification Search
None
See application file for complete search history.

(56) References Cited

U.S. PATENT DOCUMENTS

| | | |
|---|---|---|
| 5,087,616 A | 2/1992 | Myers |
| 5,225,539 A | 7/1993 | Winter |
| 5,405,940 A | 4/1995 | Boon et al. |
| 5,449,752 A | 9/1995 | Fujii et al. |
| 5,545,806 A | 8/1996 | Lonberg et al. |
| 5,569,825 A | 10/1996 | Lonberg et al. |
| 5,585,089 A | 12/1996 | Queen et al. |
| 5,639,641 A | 6/1997 | Pedersen et al. |
| 5,662,907 A | 9/1997 | Kubo et al. |
| 5,693,761 A | 12/1997 | Queen et al. |
| 5,714,352 A | 2/1998 | Jakobobits et al. |
| 6,265,150 B1 | 7/2001 | Terstappen et al. |
| 6,379,901 B1 | 4/2002 | Boon-Falleur et al. |
| 6,500,919 B1 | 12/2002 | Adema et al. |
| 6,897,288 B1 | 5/2005 | Heidecker et al. |
| 8,951,747 B2 | 2/2015 | Demotte et al. |
| 2002/0045241 A1 | 4/2002 | Schendel |
| 2002/0197266 A1 | 12/2002 | Debinski |
| 2007/0184444 A1 | 8/2007 | Abbas et al. |
| 2010/0273213 A1 | 10/2010 | Mineno et al. |
| 2011/0158957 A1 | 6/2011 | Bonini et al. |
| 2013/0115199 A1 | 5/2013 | Shiku et al. |

FOREIGN PATENT DOCUMENTS

| | | | |
|---|---|---|---|
| EP | 0 239 400 B1 | 8/1994 | |
| GB | 2 188 638 A | 10/1987 | |
| JP | H07-278193 A | 10/1995 | |
| JP | H08-500837 A | 1/1996 | |
| JP | H10-99086 A | 4/1998 | |
| JP | 2008/263950 A | 11/2008 | |
| WO | WO 91/09623 A1 | 7/1991 | |
| WO | WO 00/31239 A1 | 6/2000 | |
| WO | WO-0129220 A2 * | 4/2001 | ............... A61P 35/00 |
| WO | WO-0174847 A2 * | 10/2001 | ......... C07K 14/4748 |
| WO | WO-2007017201 A1 * | 2/2007 | ........... C12N 5/0639 |
| WO | WO 2007/032255 A1 | 3/2007 | |

(Continued)

OTHER PUBLICATIONS

Schumacher (Nat Rev Immunol. Jul. 2002;2(7):512-9). (Year: 2002).*
Uckert et al. (Cancer Immunol Immunother (2009) 58:809-822). (Year: 2009).*

(Continued)

*Primary Examiner* — Zachary S Skelding
(74) *Attorney, Agent, or Firm* — Leydig, Voit & Mayer

(57) ABSTRACT

The invention provides an isolated or purified T cell receptor (TCR) having antigenic specificity for a) melanoma antigen family A (MAGE A)-3 in the context of HLA-A1 or b) MAGE-A12 in the context of HLA-Cw7. The invention further provides related polypeptides and proteins, as well as related nucleic acids, recombinant expression vectors, host cells, and populations of cells. Further provided by the invention are antibodies, or an antigen binding portion thereof, and pharmaceutical compositions relating to the TCRs of the invention. Methods of detecting the presence of cancer in a host and methods of treating or preventing cancer in a host are further provided by the invention.

26 Claims, 14 Drawing Sheets

Specification includes a Sequence Listing.

(56) References Cited

FOREIGN PATENT DOCUMENTS

| WO | WO 2009/051555 A2 | 4/2009 | |
|---|---|---|---|
| WO | WO-2010075417 A1 * | 7/2010 | ......... C07K 14/7051 |
| WO | WO 2010/088160 A1 | 8/2010 | |
| WO | WO-2010088160 A1 * | 8/2010 | ........... C07K 14/705 |
| WO | WO 2010/133828 A1 | 11/2010 | |
| WO | WO 2012/013913 A1 | 2/2012 | |
| WO | WO-2012017081 A1 * | 2/2012 | .............. A61P 37/06 |
| WO | WO 2012/054825 A1 | 4/2012 | |
| WO | WO 2013/039889 A1 | 3/2013 | |

OTHER PUBLICATIONS

Seitz et al. (Proc Natl Acad Sci U S A. Aug. 8, 2006;103(32):12057-62). (Year: 2006).*
Yang et al. (Gene Therapy (2008) 15, 1411-1423). (Year: 2008).*
Robins et al., Blood. 2009;114:4099-4107. (Year: 2009).*
Woodsworth et al., Genome Medicine 2013, 5:98. (Year: 2013).*
Kloosterboer et al. (Leukemia (2004) 18, 798-808). (Year: 2004).*
Bettinotti et al., "Clinical and immunological evaluation of patients with metastatic melanoma undergoing immunization with the HLA-Cw*0702-associated epitope MAGE-A12:170-178." *Int. J. Cancer*, 105: 210-216 (2003).
Bluman et al., "Lysis of Human Chondrosarcoma Cells by Cytolytic T Lymphocytes Recognizing a MAGE-A3 Antigen Presented by HLA-A1 Molecules," *Journal of Orthopaedic Research*, pp. 678-684 (2007).
Carrasco et al., "Vaccination of a melanoma patient with mature dendritic cells pulsed with MAGE-3 peptides triggers the activity of nonvaccine anti-tumor cells," *J. Immunol.*, 180: 3585-3593 (2008).
Chinnasamy et al., "A TCR targeting the HLA-A*0201-restricted epitope of MAGE-A3 recognizes multiple epitopes of the MAGE-A antigen superfamily in several types of cancer," *J. Immunol.*, 186: 685-696 (2011).
Choi et al., "Synthesis and assembly of a cholera toxin B subunit-rotavirus VP7 fusion protein in transgenic potato," *Mol. Biotech.*, 31: 193-202 (2005).
Connerotte et al., "Functions of anti-MAGE t-cells induced in melanoma patients under different vaccination modalities," *Cancer Res.*, 68(10): 3931-3940 (2008).
Cooper et al., "Transfer of specificity for human immunodeficiency virus type I into primary human T lymphocytes by introduction of T-cell receptor genes ," *J. Virol*, 74: 8207-8212 (2000).
Database Accession ATT 35254, "Human T-cell receptor alpha-chain protein SEQ ID: 49," (2009).
Gaugler et al., "Human gene MAGE-3 codes for an antigen recognized on a melanoma by autlogous cytolytic T lymphocytes," *J. Experimental medicine*, 179(3): 921-930 (1994).
Groeper et al., "Cancer/testis antigen expression and specific cytotoxic T lymphocyte responses in non small cell lung cancer," *Int. J. Cancer*, 120: 337-343 (2006).
Haskard et al., "The production of human monoclonal autoantibodies from patients with rheumatoid arthritis by the ebv-hybridoma technique," *J. Immunol. Methods*, 74: 361-367 (1984).
Heidecker et al., "Cytolytic T lymphocytes raised against a human bladder carcinoma recognize an antigen encoded by gene MAGE-A12$^1$," J. Immunol., 164: 6041-6045 (2000).
Hudecz, F., "Synthesis of peptide bioconjugates," *Methods Mol. Biol.*, 298: 209-223 (2005).
Huse et al., "Generation of a large combinatorial library of the immunoglobulin repertoire in phage lambda," *Science*, 246: 1275-1281 (1989).
International Search Report, International Application No. PCT/US2012/054623 dated Feb. 13, 2013.
Johnson et al., "Gene therapy with human and mouse T-cell receptors mediates cancer regression ad targets normal tissues expressing cognate antigen," *Blood*, 114(3): 535-546 (2009).
Karanikas et al., "Monoclonal anti-MAGE-3 CTL responses in melanoma patients displaying tumor regression after vaccination with a recombinant canarypox virus," *J. Immunol.*, 171: 4898-4904 (2003).
Kazaks et al., "Melanoma vaccine candidates from chimeric hepatitis B core virus-like particles carrying a tumor-associated MAGE-3 epitope," *Biotechnol. J.*, 3(11): 1429-1436 (2008).
Kirin et al., "Amino acid and peptide bioconjugates of copper(II) and zinc(II) complexes with a modified N,N-bis(2-picolyl)amine ligand," *Inorg. Chem.*, 44: 5405-5415 (2005).
Köhler et al., "Derivation of specific antibody-producing tissue culture and tumor lines by cell fusion," *Eur. J. Immunol.*, 6(7), 511-519 (1976).
Laydon et al., "Estimating T-cell repertoire diversity: limitations of classical estimators and a new approach," *Phil. Trans. R. Soc. B.*, 370: 1-11 (2015).
Myc et al., "Cancer Vaccines. Any Future?," *Arch. Immunol. Ther. Exp.*, 59: 249-259 (2011).
Panelli et al., "A tumor-infiltrating lymphocyte from a melanoma metastasis with decreased expression of melanoma differentiation antigens recognizes MAGE-12," *J. Immunol.*, 164: 4382-4392 (2000).
Parmentier et al., "Production of an antigenic peptide by insulin-degrading enzyme," *Nature Immunology*, 11: 449-454 (2010).
Pedersen et al., "Comparison of surface accessible residues in human and murine immunoglobulin fv domains," *J. Mol. Biol.*, 235: 959-973 (1994).
Quinn et al., "International society for cell and gene therapy of cancer 2009 annual meeting held in Cork, Ireland," *Human Gene Therapy*, 21: 9-26 (2010).
Reiter et al., "Engineering interchain disulfide bonds into conserved framework regions of fv fragments: improved biochemical characteristics of recombinant immunotoxins containing disulfide-stabilized fv," *Protein Eng.*, 7(5): 697-704 (1994).
Robbins et al., "Tumor regression in patients with metastatic synovial cell sarcoma and melanoma using genetically engineered lymphocytes reactive with NY-ESO-1," *J. Clin. Oncol.*, 29: 917-924 (2011).
Roder et al., "The EBV-hybridoma technique," *Methods Enzymol.*, 121: 140-167 (1986).
Schaft et al., "Peptide fine specificity of anti-glycoprotein 100 CTL is preserved following transfer of engineered TCR αβ genes into primary human T lymphocytes," *J. Immunol.*, 170: 2186-2194 (2003).
Schultz et al., "A MAGE-3 peptide recognized on HLA-B35 and HLA-A1 by cytolytic T lymphocytes," *Tissue Antigens*, 57: 103-109 (2001).
Sebestyen et al., "Human TCR That Incorporate CD3ζ Induce Highly Preferred Pairing between TCR α and β Chains following Gene Transfer," *J. Immunol.*, 180: 7736-7746 (2008).
Thomas et al., "Human T cells expressing affinity-matured TCR display accelerated responses but fail to recognize low density of MHC-peptide antigen," *Blood*, 118(2): 319-329 (2011).
Thomas et al., "Molecular immunology lessons from therapeutic T-cell receptor gene transfer," *Immunology*, 129(2): 170-177 (2010).
Van Baren et al., "Tumoral and Immunologic Response After Vaccination of Melanoma Patients With an ALVAC Virus Encoding MAGE Antigens Recognized by T Cells," *J. Clin. Oncology*, 23(35): 9008-9021 (2005).
Viola et al., "T cell activation determined by T cell receptor No. and tunable thresholds," *Science*, 273: 104-106 (1996).
Wadhwa et al., "Receptor mediated glycotargeting," *J. Drug Targeting*, 3: 111-127 (1995).
Weijtens et al., "Functional balance between T cell chimeric receptor density and tumor associated antigen density: CTL mediated cytolysis and lymphokine production," *Gene Ther.*, 7: 35-42 (2000).
Written Opinion, International Application No. PCT/US2012/054623 dated Feb. 13, 2013.
Zhu et al., "Characterization of T-cell receptors directed against HLA-A*01-restricted and C*07-restricted epitopes of MAGE-A3 and MAGE-A12," *J. Immunother.*, 35(9): 680-688 (2012).
Database Accession AAS64170, "Human T-cell receptor Vb chain 4E5 for prostate protein P501S cDNA," (2002).

(56) References Cited

OTHER PUBLICATIONS

Database Accession ADU98589, "Lung tumor antigen L762P TCR clone Vbeta DNA Seq ID No. 440" (2005).
"TRA T-cell receptor alpha locus [*Homo sapiens* (human)]," Gene ID: 6955, (updated Oct. 9, 2016), Entrez Gene (ncbi.nlm.nih.gov/gene), printed on Dec. 8, 2016.
"TRB T cell receptor beta locus [*Homo sapiens* (human)]," Gene ID: 6957, (updated Oct. 9, 2016), Entrez Gene (ncbi.nlm.nih.gov/gene), printed on Dec. 8, 2016.
Clay et al., "Efficient Transfer of a Tumor Antigen-Reactive TCR to Human Peripheral Blood Lymphocytes Confers Anti-Tumor Reactivity," *J. Immunol.*, 163(1), 507-513 (1999).
Murphy, et al., *Janeway's Immunobiology*, Garland Science, Taylor & Francis Group, LLC, 7th Ed., 157-158 (2008).
U.S. Appl. No. 14/344,354, filed Mar. 12, 2014.
U.S. Appl. No. 14/344,354, filed Sep. 11, 2012.
U.S. Appl. No. 14/344,354, filed Apr. 22, 2014.

\* cited by examiner

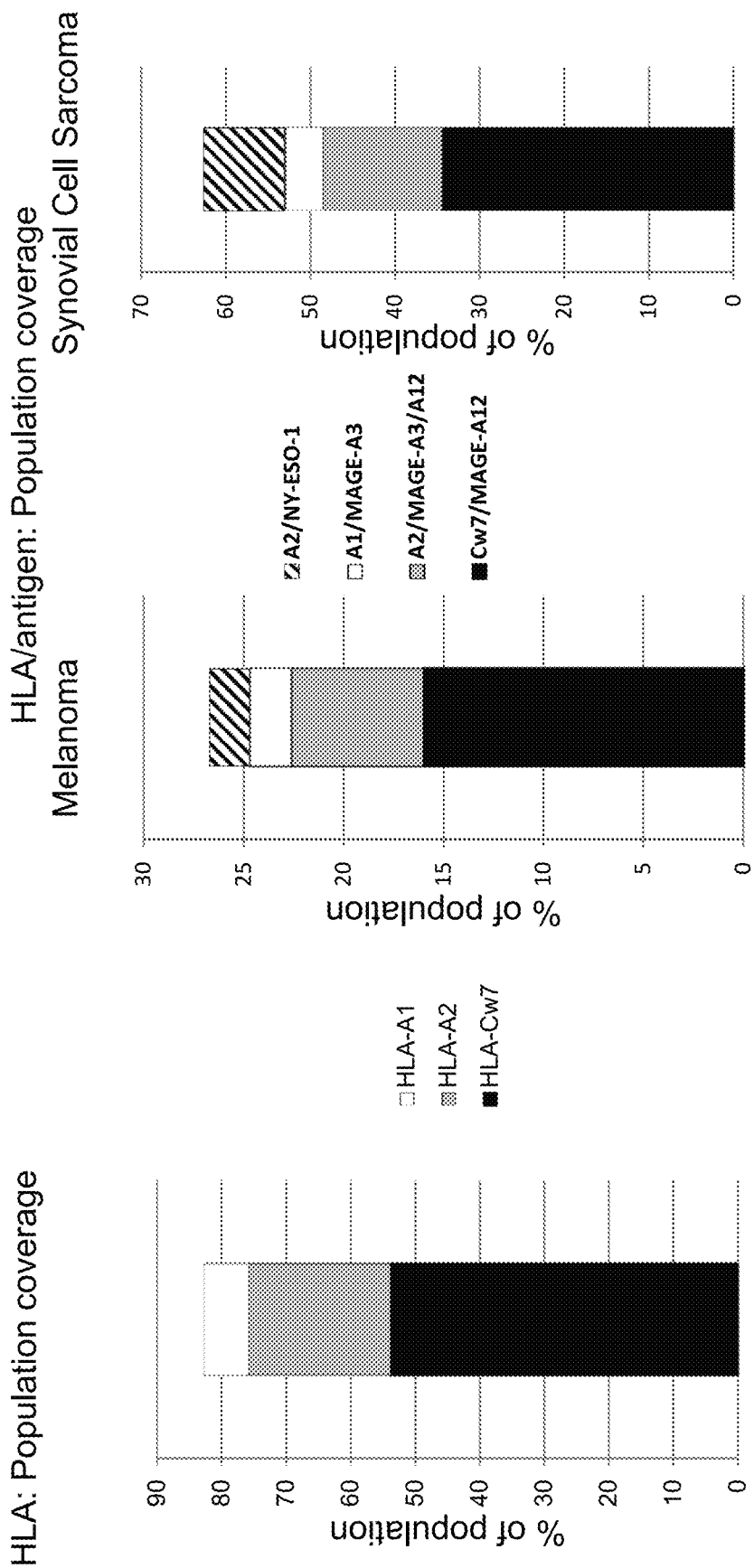

SEQUENCE LISTING

<160> NUMBER OF SEQ ID NOS: 63

<210> SEQ ID NO 1
<211> LENGTH: 314
<212> TYPE: PRT
<213> ORGANISM: Homo sapiens

<400> SEQUENCE: 1

```
Met Pro Leu Glu Gln Arg Ser Gln His Cys Lys Pro Glu Glu Gly Leu
 1               5                  10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
        35                  40                  45

Thr Leu Gly Glu Val Pro Ala Ala Glu Ser Pro Asp Pro Pro Gln Ser
 50                  55                  60

Pro Gln Gly Ala Ser Ser Leu Pro Thr Thr Met Asn Tyr Pro Leu Trp
 65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
            115                 120                 125

Pro Val Thr Lys Ala Glu Met Leu Gly Ser Val Val Gly Asn Trp Gln
        130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205

Ile Ala Arg Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Gly Pro His Ile Ser Tyr Pro Pro Leu
    290                 295                 300

His Glu Trp Val Leu Arg Glu Gly Glu Glu
305                 310
```

<210> SEQ ID NO 2
<211> LENGTH: 9
<212> TYPE: PRT
<213> ORGANISM: Homo sapiens

<400> SEQUENCE: 2

Glu Val Asp Pro Ile Gly His Leu Tyr

<210> SEQ ID NO 3
<211> LENGTH: 314
<212> TYPE: PRT
<213> ORGANISM: Homo sapiens

<400> SEQUENCE: 3

Met Pro Leu Glu Gln Arg Ser Gln His Cys Lys Pro Glu Gly Leu
1               5                   10                  15

Glu Ala Gln Gly Glu Ala Leu Gly Leu Val Gly Ala Gln Ala Pro Ala
                20                  25                  30

Thr Glu Gln Glu Thr Ala Ser Ser Ser Thr Leu Val Glu Val
            35                  40                  45

Thr Leu Arg Glu Val Pro Ala Ala Glu Ser Pro Ser Pro Pro His Ser
    50                  55                  60

Pro Gln Gly Ala Ser Thr Leu Pro Thr Thr Ile Asn Tyr Thr Leu Trp
65                  70                  75                  80

Ser Gln Ser Asp Glu Gly Ser Ser Asn Glu Gln Glu Gly Pro Ser
                85                  90                  95

Thr Phe Pro Asp Leu Glu Thr Ser Phe Gln Val Ala Leu Ser Arg Lys
            100                 105                 110

Met Ala Glu Leu Val His Phe Leu Leu Leu Lys Tyr Arg Ala Arg Glu
            115                 120                 125

Pro Phe Thr Lys Ala Glu Met Leu Gly Ser Val Ile Arg Asn Phe Gln
    130                 135                 140

Asp Phe Phe Pro Val Ile Phe Ser Lys Ala Ser Glu Tyr Leu Gln Leu
145                 150                 155                 160

Val Phe Gly Ile Glu Val Val Glu Val Val Arg Ile Gly His Leu Tyr
                165                 170                 175

Ile Leu Val Thr Cys Leu Gly Leu Ser Tyr Asp Gly Leu Leu Gly Asp
            180                 185                 190

Asn Gln Ile Val Pro Lys Thr Gly Leu Leu Ile Ile Val Leu Ala Ile
        195                 200                 205

Ile Ala Lys Glu Gly Asp Cys Ala Pro Glu Glu Lys Ile Trp Glu Glu
    210                 215                 220

Leu Ser Val Leu Glu Ala Ser Asp Gly Arg Glu Asp Ser Val Phe Ala
225                 230                 235                 240

His Pro Arg Lys Leu Leu Thr Gln Asp Leu Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Leu Leu Lys Ile Ser Gly Gly Pro His Ile Ser Tyr Pro Pro Leu
    290                 295                 300

His Glu Trp Ala Phe Arg Glu Gly Glu Glu
305                 310

<210> SEQ ID NO 4
<211> LENGTH: 9
<212> TYPE: PRT
<213> ORGANISM: Homo sapiens

<400> SEQUENCE: 4

Val Arg Ile Gly His Leu Tyr Ile Leu

```
<210> SEQ ID NO 5
<211> LENGTH: 6
<212> TYPE: PRT
<213> ORGANISM: Homo sapiens

<400> SEQUENCE: 5

Asn Ser Ala Ser Gln Ser
1               5

<210> SEQ ID NO 6
<211> LENGTH: 6
<212> TYPE: PRT
<213> ORGANISM: Homo sapiens

<400> SEQUENCE: 6

Val Tyr Ser Ser Gly Asn
1               5

<210> SEQ ID NO 7
<211> LENGTH: 9
<212> TYPE: PRT
<213> ORGANISM: Homo sapiens

<400> SEQUENCE: 7

Val Val Asn Arg Asp Asn Asp Met Arg
1               5

<210> SEQ ID NO 8
<211> LENGTH: 5
<212> TYPE: PRT
<213> ORGANISM: Homo sapiens

<400> SEQUENCE: 8

Lys Gly His Asp Arg
1               5

<210> SEQ ID NO 9
<211> LENGTH: 6
<212> TYPE: PRT
<213> ORGANISM: Homo sapiens

<400> SEQUENCE: 9

Ser Phe Asp Val Lys Asp
1               5

<210> SEQ ID NO 10
<211> LENGTH: 12
<212> TYPE: PRT
<213> ORGANISM: Homo sapiens

<400> SEQUENCE: 10

Ala Thr Ser Glu Gly Gly Pro Pro Tyr Glu Gln Tyr
1               5                   10

<210> SEQ ID NO 11
<211> LENGTH: 129
<212> TYPE: PRT
<213> ORGANISM: Homo sapiens

<400> SEQUENCE: 11

Met Ile Ser Leu Arg Val Leu Leu Val Ile Leu Trp Leu Gln Leu Ser
1               5                   10                  15
```

```
Trp Val Trp Ser Gln Arg Lys Glu Val Glu Gln Asp Pro Gly Pro Phe
            20                  25                  30

Asn Val Pro Glu Gly Ala Thr Val Ala Phe Asn Cys Thr Tyr Ser Asn
            35                  40                  45

Ser Ala Ser Gln Ser Phe Phe Trp Tyr Arg Gln Asp Cys Arg Lys Glu
50                  55                  60

Pro Lys Leu Leu Met Ser Val Tyr Ser Ser Gly Asn Glu Asp Gly Arg
65                  70                  75                  80

Phe Thr Ala Gln Leu Asn Arg Ala Ser Gln Tyr Ile Ser Leu Leu Ile
                85                  90                  95

Arg Asp Ser Lys Leu Ser Asp Ser Ala Thr Tyr Leu Cys Val Val Asn
            100                 105                 110

Arg Asp Asn Asp Met Arg Phe Gly Ala Gly Thr Arg Leu Thr Val Lys
            115                 120                 125

Pro

<210> SEQ ID NO 12
<211> LENGTH: 132
<212> TYPE: PRT
<213> ORGANISM: Homo sapiens

<400> SEQUENCE: 12

Met Ala Ser Leu Leu Phe Phe Cys Gly Ala Phe Tyr Leu Leu Gly Thr
1               5                   10                  15

Gly Ser Met Asp Ala Asp Val Thr Gln Thr Pro Arg Asn Arg Ile Thr
            20                  25                  30

Lys Thr Gly Lys Arg Ile Met Leu Glu Cys Ser Gln Thr Lys Gly His
            35                  40                  45

Asp Arg Met Tyr Trp Tyr Arg Gln Asp Pro Gly Leu Gly Leu Arg Leu
50                  55                  60

Ile Tyr Tyr Ser Phe Asp Val Lys Asp Ile Asn Lys Gly Glu Ile Ser
65                  70                  75                  80

Asp Gly Tyr Ser Val Ser Arg Gln Ala Gln Ala Lys Phe Ser Leu Ser
                85                  90                  95

Leu Glu Ser Ala Ile Pro Asn Gln Thr Ala Leu Tyr Phe Cys Ala Thr
            100                 105                 110

Ser Glu Gly Gly Pro Pro Tyr Glu Gln Tyr Phe Gly Pro Gly Thr Arg
            115                 120                 125

Leu Thr Val Thr
130

<210> SEQ ID NO 13
<211> LENGTH: 270
<212> TYPE: PRT
<213> ORGANISM: Homo sapiens

<400> SEQUENCE: 13

Met Ile Ser Leu Arg Val Leu Leu Val Ile Leu Trp Leu Gln Leu Ser
1               5                   10                  15

Trp Val Trp Ser Gln Arg Lys Glu Val Glu Gln Asp Pro Gly Pro Phe
            20                  25                  30

Asn Val Pro Glu Gly Ala Thr Val Ala Phe Asn Cys Thr Tyr Ser Asn
            35                  40                  45

Ser Ala Ser Gln Ser Phe Phe Trp Tyr Arg Gln Asp Cys Arg Lys Glu
50                  55                  60

Pro Lys Leu Leu Met Ser Val Tyr Ser Ser Gly Asn Glu Asp Gly Arg
```

```
                65                  70                  75                  80
        Phe Thr Ala Gln Leu Asn Arg Ala Ser Gln Tyr Ile Ser Leu Leu Ile
                        85                  90                  95

Arg Asp Ser Lys Leu Ser Asp Ser Ala Thr Tyr Leu Cys Val Val Asn
                        100                 105                 110

Arg Asp Asn Asp Met Arg Phe Gly Ala Gly Thr Arg Leu Thr Val Lys
                        115                 120                 125

Pro Asn Ile Gln Asn Pro Asp Pro Ala Val Tyr Gln Leu Arg Asp Ser
                        130                 135                 140

Lys Ser Ser Asp Lys Ser Val Cys Leu Phe Thr Asp Ile Asp Ser Gln
        145                 150                 155                 160

Thr Asn Val Ser Gln Ser Lys Asp Ser Asp Val Tyr Ile Thr Asp Lys
                        165                 170                 175

Thr Val Leu Asp Met Arg Ser Met Asp Phe Lys Ser Asn Ser Ala Val
                        180                 185                 190

Ala Trp Ser Asn Lys Ser Asp Phe Ala Cys Ala Asn Ala Phe Asn Asn
                        195                 200                 205

Ser Ile Ile Pro Glu Asp Thr Phe Phe Pro Ser Pro Glu Ser Ser Cys
                        210                 215                 220

Asp Val Lys Leu Val Glu Lys Ser Phe Glu Thr Asp Thr Asn Leu Asn
        225                 230                 235                 240

Phe Gln Asn Leu Ser Val Ile Gly Phe Arg Ile Leu Leu Leu Lys Val
                        245                 250                 255

Ala Gly Phe Asn Leu Leu Met Thr Leu Arg Leu Trp Ser Ser
                        260                 265                 270

<210> SEQ ID NO 14
<211> LENGTH: 311
<212> TYPE: PRT
<213> ORGANISM: Homo sapiens

<400> SEQUENCE: 14

Met Ala Ser Leu Leu Phe Phe Cys Gly Ala Phe Tyr Leu Leu Gly Thr
1               5                   10                  15

Gly Ser Met Asp Ala Asp Val Thr Gln Thr Pro Arg Asn Arg Ile Thr
                20                  25                  30

Lys Thr Gly Lys Arg Ile Met Leu Glu Cys Ser Gln Thr Lys Gly His
                35                  40                  45

Asp Arg Met Tyr Trp Tyr Arg Gln Asp Pro Gly Leu Gly Leu Arg Leu
        50                  55                  60

Ile Tyr Tyr Ser Phe Asp Val Lys Asp Ile Asn Lys Gly Glu Ile Ser
65                  70                  75                  80

Asp Gly Tyr Ser Val Ser Arg Gln Ala Gln Ala Lys Phe Ser Leu Ser
                85                  90                  95

Leu Glu Ser Ala Ile Pro Asn Gln Thr Ala Leu Tyr Phe Cys Ala Thr
                100                 105                 110

Ser Glu Gly Gly Pro Pro Tyr Glu Gln Tyr Phe Gly Pro Gly Thr Arg
                115                 120                 125

Leu Thr Val Thr Glu Asp Leu Lys Asn Val Phe Pro Pro Glu Val Ala
                130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175
```

```
Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 15
<211> LENGTH: 27
<212> TYPE: PRT
<213> ORGANISM: Homo sapiens

<400> SEQUENCE: 15

Arg Ala Lys Arg Ser Gly Ser Gly Ala Thr Asn Phe Ser Leu Leu Lys
1               5                   10                  15

Gln Ala Gly Asp Val Glu Glu Asn Pro Gly Pro
            20                  25

<210> SEQ ID NO 16
<211> LENGTH: 6
<212> TYPE: PRT
<213> ORGANISM: Homo sapiens

<400> SEQUENCE: 16

Asn Ser Ala Phe Gln Tyr
1               5

<210> SEQ ID NO 17
<211> LENGTH: 6
<212> TYPE: PRT
<213> ORGANISM: Homo sapiens

<400> SEQUENCE: 17

Thr Tyr Ser Ser Gly Asn
1               5

<210> SEQ ID NO 18
<211> LENGTH: 9
<212> TYPE: PRT
<213> ORGANISM: Homo sapiens

<400> SEQUENCE: 18

Ala Met Arg Gly Ala Gln Lys Leu Val
1               5

<210> SEQ ID NO 19
<211> LENGTH: 5
<212> TYPE: PRT
<213> ORGANISM: Homo sapiens
```

<400> SEQUENCE: 19

Leu Asn His Asn Val
1               5

<210> SEQ ID NO 20
<211> LENGTH: 6
<212> TYPE: PRT
<213> ORGANISM: Homo sapiens

<400> SEQUENCE: 20

Tyr Tyr Asp Lys Asp Phe
1               5

<210> SEQ ID NO 21
<211> LENGTH: 11
<212> TYPE: PRT
<213> ORGANISM: Homo sapiens

<400> SEQUENCE: 21

Ala Thr Ser Trp Asp Arg Gly Tyr Glu Gln Tyr
1               5                   10

<210> SEQ ID NO 22
<211> LENGTH: 131
<212> TYPE: PRT
<213> ORGANISM: Homo sapiens

<400> SEQUENCE: 22

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Arg Gly Ala Gln Lys Leu Val Phe Gly Gly Gly Thr Arg Leu Thr
        115                 120                 125

Ile Asn Pro
    130

<210> SEQ ID NO 23
<211> LENGTH: 131
<212> TYPE: PRT
<213> ORGANISM: Homo sapiens

<400> SEQUENCE: 23

Met Gly Pro Gly Leu Leu His Trp Met Ala Leu Cys Leu Leu Gly Thr
1               5                   10                  15

Gly His Gly Asp Ala Met Val Ile Gln Asn Pro Arg Tyr Gln Val Thr
            20                  25                  30

Gln Phe Gly Lys Pro Val Thr Leu Ser Cys Ser Gln Thr Leu Asn His
        35                  40                  45

```
Asn Val Met Tyr Trp Tyr Gln Gln Lys Ser Ser Gln Ala Pro Lys Leu
    50                  55                  60

Leu Phe His Tyr Tyr Asp Lys Asp Phe Asn Asn Glu Ala Asp Thr Pro
65                  70                  75                  80

Asp Asn Phe Gln Ser Arg Arg Pro Asn Thr Ser Phe Cys Phe Leu Asp
                85                  90                  95

Ile Arg Ser Pro Gly Leu Gly Asp Ala Ala Met Tyr Leu Cys Ala Thr
            100                 105                 110

Ser Trp Asp Arg Gly Tyr Glu Gln Tyr Phe Gly Pro Gly Thr Arg Leu
        115                 120                 125

Thr Val Thr
    130

<210> SEQ ID NO 24
<211> LENGTH: 272
<212> TYPE: PRT
<213> ORGANISM: Homo sapiens

<400> SEQUENCE: 24

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Arg Gly Ala Gln Lys Leu Val Phe Gly Gln Gly Thr Arg Leu Thr
        115                 120                 125

Ile Asn Pro Asn Ile Gln Asn Pro Asp Pro Ala Val Tyr Gln Leu Arg
    130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Arg
            260                 265                 270
```

```
<210> SEQ ID NO 25
<211> LENGTH: 310
<212> TYPE: PRT
<213> ORGANISM: Homo sapiens

<400> SEQUENCE: 25

Met Gly Pro Gly Leu Leu His Trp Met Ala Leu Cys Leu Leu Gly Thr
1               5                   10                  15

Gly His Gly Asp Ala Met Val Ile Gln Asn Pro Arg Tyr Gln Val Thr
            20                  25                  30

Gln Phe Gly Lys Pro Val Thr Leu Ser Cys Ser Gln Thr Leu Asn His
        35                  40                  45

Asn Val Met Tyr Trp Tyr Gln Gln Lys Ser Ser Gln Ala Pro Lys Leu
    50                  55                  60

Leu Phe His Tyr Tyr Asp Lys Asp Phe Asn Asn Glu Ala Asp Thr Pro
65                  70                  75                  80

Asp Asn Phe Gln Ser Arg Arg Pro Asn Thr Ser Phe Cys Phe Leu Asp
                85                  90                  95

Ile Arg Ser Pro Gly Leu Gly Asp Ala Ala Met Tyr Leu Cys Ala Thr
            100                 105                 110

Ser Trp Asp Arg Gly Tyr Glu Gln Tyr Phe Gly Pro Gly Thr Arg Leu
        115                 120                 125

Thr Val Thr Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
225                 230                 235                 240

Thr Gln Asp Arg Ala Lys Pro Val Thr Gln Ile Val Ser Ala Glu Ala
                245                 250                 255

Trp Gly Arg Ala Asp Cys Gly Phe Thr Ser Glu Ser Tyr Gln Gln Gly
            260                 265                 270

Val Leu Ser Ala Thr Ile Leu Tyr Glu Ile Leu Leu Gly Lys Ala Thr
        275                 280                 285

Leu Tyr Ala Val Leu Val Ser Ala Leu Val Leu Met Ala Met Val Lys
    290                 295                 300

Arg Lys Asp Ser Arg Gly
305                 310

<210> SEQ ID NO 26
<211> LENGTH: 6
<212> TYPE: PRT
<213> ORGANISM: Homo sapiens

<400> SEQUENCE: 26

Asp Ser Ala Ser Asn Tyr
1               5
```

```
<210> SEQ ID NO 27
<211> LENGTH: 7
<212> TYPE: PRT
<213> ORGANISM: Homo sapiens

<400> SEQUENCE: 27

Ile Arg Ser Asn Val Gly Glu
1               5

<210> SEQ ID NO 28
<211> LENGTH: 10
<212> TYPE: PRT
<213> ORGANISM: Homo sapiens

<400> SEQUENCE: 28

Ala Ala Ser Gly Ala Thr Asp Lys Leu Ile
1               5                   10

<210> SEQ ID NO 29
<211> LENGTH: 5
<212> TYPE: PRT
<213> ORGANISM: Homo sapiens

<400> SEQUENCE: 29

Met Gly His Asp Lys
1               5

<210> SEQ ID NO 30
<211> LENGTH: 6
<212> TYPE: PRT
<213> ORGANISM: Homo sapiens

<400> SEQUENCE: 30

Ser Tyr Gly Val Asn Ser
1               5

<210> SEQ ID NO 31
<211> LENGTH: 9
<212> TYPE: PRT
<213> ORGANISM: Homo sapiens

<400> SEQUENCE: 31

Ala Ser Ser Gly Gly His Glu Gln Tyr
1               5

<210> SEQ ID NO 32
<211> LENGTH: 130
<212> TYPE: PRT
<213> ORGANISM: Homo sapiens

<400> SEQUENCE: 32

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
                20                  25                  30

Gln Glu Gly Asp Ser Ala Val Ile Lys Cys Thr Tyr Ser Asp Ser Ala
            35                  40                  45

Ser Asn Tyr Phe Pro Trp Tyr Lys Gln Glu Leu Gly Lys Arg Pro Gln
        50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95
```

```
Thr Glu Thr Gln Pro Glu Asp Ser Ala Val Tyr Phe Cys Ala Ala Ser
            100                 105                 110

Gly Ala Thr Asp Lys Leu Ile Phe Gly Thr Gly Thr Arg Leu Gln Val
        115                 120                 125

Phe Pro
    130

<210> SEQ ID NO 33
<211> LENGTH: 129
<212> TYPE: PRT
<213> ORGANISM: Homo sapiens

<400> SEQUENCE: 33

Met Thr Ile Arg Leu Leu Cys Tyr Met Gly Phe Tyr Phe Leu Gly Ala
1               5                   10                  15

Gly Leu Met Glu Ala Asp Ile Tyr Gln Thr Pro Arg Tyr Leu Val Ile
            20                  25                  30

Gly Thr Gly Lys Lys Ile Thr Leu Glu Cys Ser Gln Thr Met Gly His
        35                  40                  45

Asp Lys Met Tyr Trp Tyr Gln Gln Asp Pro Gly Met Glu Leu His Leu
    50                  55                  60

Ile His Tyr Ser Tyr Gly Val Asn Ser Thr Glu Lys Gly Asp Leu Ser
65                  70                  75                  80

Ser Glu Ser Thr Val Ser Arg Ile Arg Thr Glu His Phe Pro Leu Thr
                85                  90                  95

Leu Glu Ser Ala Arg Pro Ser His Thr Ser Gln Tyr Leu Cys Ala Ser
            100                 105                 110

Ser Gly Gly His Glu Gln Tyr Phe Gly Pro Gly Thr Arg Leu Thr Val
        115                 120                 125

Thr

<210> SEQ ID NO 34
<211> LENGTH: 271
<212> TYPE: PRT
<213> ORGANISM: Homo sapiens

<400> SEQUENCE: 34

Met Thr Ser Ile Arg Ala Val Phe Ile Phe Leu Trp Leu Gln Leu Asp
1               5                   10                  15

Leu Val Asn Gly Glu Asn Val Glu Gln His Pro Ser Thr Leu Ser Val
            20                  25                  30

Gln Glu Gly Asp Ser Ala Val Ile Lys Cys Thr Tyr Ser Asp Ser Ala
        35                  40                  45

Ser Asn Tyr Phe Pro Trp Tyr Lys Gln Glu Leu Gly Lys Arg Pro Gln
    50                  55                  60

Leu Ile Ile Asp Ile Arg Ser Asn Val Gly Glu Lys Lys Asp Gln Arg
65                  70                  75                  80

Ile Ala Val Thr Leu Asn Lys Thr Ala Lys His Phe Ser Leu His Ile
                85                  90                  95

Thr Glu Thr Gln Pro Glu Asp Ser Ala Val Tyr Phe Cys Ala Ala Ser
            100                 105                 110

Gly Ala Thr Asp Lys Leu Ile Phe Gly Thr Gly Thr Arg Leu Gln Val
        115                 120                 125

Phe Pro Asn Ile Gln Asn Pro Asp Pro Ala Val Tyr Gln Leu Arg Asp
    130                 135                 140
```

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
            165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
        195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 35
<211> LENGTH: 308
<212> TYPE: PRT
<213> ORGANISM: Homo sapiens

<400> SEQUENCE: 35

Met Thr Ile Arg Leu Leu Cys Tyr Met Gly Phe Tyr Phe Leu Gly Ala
1               5                   10                  15

Gly Leu Met Glu Ala Asp Ile Tyr Gln Thr Pro Arg Tyr Leu Val Ile
            20                  25                  30

Gly Thr Gly Lys Lys Ile Thr Leu Glu Cys Ser Gln Thr Met Gly His
            35                  40                  45

Asp Lys Met Tyr Trp Tyr Gln Gln Asp Pro Gly Met Glu Leu His Leu
        50                  55                  60

Ile His Tyr Ser Tyr Gly Val Asn Ser Thr Glu Lys Gly Asp Leu Ser
65                  70                  75                  80

Ser Glu Ser Thr Val Ser Arg Ile Arg Thr Glu His Phe Pro Leu Thr
                85                  90                  95

Leu Glu Ser Ala Arg Pro Ser His Thr Ser Gln Tyr Leu Cys Ala Ser
            100                 105                 110

Ser Gly His Glu Gln Tyr Phe Gly Pro Gly Thr Arg Leu Thr Val
            115                 120                 125

Thr Glu Asp Leu Lys Asn Val Phe Pro Pro Glu Val Ala Val Phe Glu
130                 135                 140

Pro Ser Glu Ala Glu Ile Ser His Thr Gln Lys Ala Thr Leu Val Cys
145                 150                 155                 160

Leu Ala Thr Gly Phe Phe Pro Asp His Val Glu Leu Ser Trp Trp Val
                165                 170                 175

Asn Gly Lys Glu Val His Ser Gly Val Ser Thr Asp Pro Gln Pro Leu
            180                 185                 190

Lys Glu Gln Pro Ala Leu Asn Asp Ser Arg Tyr Cys Leu Ser Ser Arg
        195                 200                 205

Leu Arg Val Ser Ala Thr Phe Trp Gln Asn Pro Arg Asn His Phe Arg
210                 215                 220

Cys Gln Val Gln Phe Tyr Gly Leu Ser Glu Asn Asp Glu Trp Thr Gln
225                 230                 235                 240

Asp Arg Ala Lys Pro Val Thr Gln Ile Val Ser Ala Glu Ala Trp Gly
                245                 250                 255

Arg Ala Asp Cys Gly Phe Thr Ser Val Ser Tyr Gln Gln Gly Val Leu
            260                 265                 270

Ser Ala Thr Ile Leu Tyr Glu Ile Leu Leu Gly Lys Ala Thr Leu Tyr
        275                 280                 285

Ala Val Leu Val Ser Ala Leu Val Leu Met Ala Met Val Lys Arg Lys
    290                 295                 300

Asp Ser Arg Gly
305

<210> SEQ ID NO 36
<211> LENGTH: 7
<212> TYPE: PRT
<213> ORGANISM: Homo sapiens

<400> SEQUENCE: 36

Thr Ser Glu Ser Asp Tyr Tyr
1               5

<210> SEQ ID NO 37
<211> LENGTH: 8
<212> TYPE: PRT
<213> ORGANISM: Homo sapiens

<400> SEQUENCE: 37

Gln Glu Ala Tyr Lys Gln Gln Asn
1               5

<210> SEQ ID NO 38
<211> LENGTH: 13
<212> TYPE: PRT
<213> ORGANISM: Homo sapiens

<400> SEQUENCE: 38

Ala Tyr Arg Ser Ala Gln Gly Gly Ser Glu Lys Leu Val
1               5                   10

<210> SEQ ID NO 39
<211> LENGTH: 5
<212> TYPE: PRT
<213> ORGANISM: Homo sapiens

<400> SEQUENCE: 39

Leu Gly His Asn Ala
1               5

<210> SEQ ID NO 40
<211> LENGTH: 6
<212> TYPE: PRT
<213> ORGANISM: Homo sapiens

<400> SEQUENCE: 40

Tyr Ser Leu Glu Glu Arg
1               5

<210> SEQ ID NO 41
<211> LENGTH: 12
<212> TYPE: PRT
<213> ORGANISM: Homo sapiens

<400> SEQUENCE: 41

Ala Ser Ser Gln Thr Thr Tyr Tyr Asn Glu Gln Phe
1               5                   10

<210> SEQ ID NO 42
<211> LENGTH: 137
<212> TYPE: PRT
<213> ORGANISM: Homo sapiens

<400> SEQUENCE: 42

```
Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Tyr Arg Ser Ala Gln Gly Gly Ser Glu Lys Leu Val Phe Gly Lys
        115                 120                 125

Gly Thr Lys Leu Thr Val Asn Pro Tyr
    130                 135
```

<210> SEQ ID NO 43
<211> LENGTH: 132
<212> TYPE: PRT
<213> ORGANISM: Homo sapiens

<400> SEQUENCE: 43

```
Met Gly Cys Arg Leu Leu Cys Cys Ala Val Leu Cys Leu Leu Gly Ala
1               5                   10                  15

Val Pro Met Glu Thr Gly Val Thr Gln Thr Pro Arg His Leu Val Met
            20                  25                  30

Gly Met Thr Asn Lys Lys Ser Leu Lys Cys Glu Gln His Leu Gly His
        35                  40                  45

Asn Ala Met Tyr Trp Tyr Lys Gln Ser Ala Lys Lys Pro Leu Glu Leu
    50                  55                  60

Met Phe Val Tyr Ser Leu Glu Glu Arg Val Glu Asn Asn Ser Val Pro
65                  70                  75                  80

Ser Arg Phe Ser Pro Glu Cys Pro Asn Ser Ser His Leu Phe Leu His
                85                  90                  95

Leu His Thr Leu Gln Pro Glu Asp Ser Ala Leu Tyr Leu Cys Ala Ser
            100                 105                 110

Ser Gln Thr Thr Tyr Tyr Asn Glu Gln Phe Phe Gly Pro Gly Thr Arg
        115                 120                 125

Leu Thr Val Leu
    130
```

<210> SEQ ID NO 44
<211> LENGTH: 277
<212> TYPE: PRT
<213> ORGANISM: Homo sapiens

<400> SEQUENCE: 44

```
Met Ala Cys Pro Gly Phe Leu Trp Ala Leu Val Ile Ser Thr Cys Leu
```

```
            1               5                  10                 15
        Glu Phe Ser Met Ala Gln Thr Val Thr Gln Ser Gln Pro Glu Met Ser
                        20                 25                 30

Val Gln Glu Ala Glu Thr Val Thr Leu Ser Cys Thr Tyr Asp Thr Ser
                        35                 40                 45

Glu Ser Asp Tyr Tyr Leu Phe Trp Tyr Lys Gln Pro Pro Ser Arg Gln
                        50                 55                 60

Met Ile Leu Val Ile Arg Gln Glu Ala Tyr Lys Gln Asn Ala Thr
         65                 70                 75                 80

Glu Asn Arg Phe Ser Val Asn Phe Gln Lys Ala Ala Lys Ser Phe Ser
                        85                 90                 95

Leu Lys Ile Ser Asp Ser Gln Leu Gly Asp Ala Ala Met Tyr Phe Cys
                        100                105                110

Ala Tyr Arg Ser Ala Gln Gly Gly Ser Glu Lys Leu Val Phe Gly Lys
                        115                120                125

Gly Thr Lys Leu Thr Val Asn Pro Tyr Ile Gln Asn Pro Asp Pro Ala
         130                135                140

Val Tyr Gln Leu Arg Asp Ser Lys Ser Ser Asp Lys Ser Val Cys Leu
        145                 150                155                160

Phe Thr Asp Phe Asp Ser Gln Thr Asn Val Ser Gln Ser Lys Asp Ser
                        165                170                175

Asp Val Tyr Ile Thr Asp Lys Thr Val Leu Asp Met Arg Ser Met Asp
                        180                185                190

Phe Lys Ser Asn Ser Ala Val Ala Trp Ser Asn Lys Ser Asp Phe Ala
                        195                200                205

Cys Ala Asn Ala Phe Asn Asn Ser Ile Ile Pro Glu Asp Thr Phe Phe
                        210                215                220

Pro Ser Pro Glu Ser Ser Cys Asp Val Lys Leu Val Glu Lys Ser Phe
        225                 230                235                240

Glu Thr Asp Thr Asn Leu Asn Phe Gln Asn Leu Ser Val Ile Gly Phe
                        245                250                255

Arg Ile Leu Leu Leu Lys Val Ala Gly Phe Asn Leu Leu Met Thr Leu
                        260                265                270

Arg Leu Trp Ser Ser
                        275

<210> SEQ ID NO 45
<211> LENGTH: 311
<212> TYPE: PRT
<213> ORGANISM: Homo sapiens

<400> SEQUENCE: 45

Met Gly Cys Arg Leu Leu Cys Cys Ala Val Leu Cys Leu Leu Gly Ala
         1               5                  10                 15

Val Pro Met Glu Thr Gly Val Thr Gln Thr Pro Arg His Leu Val Met
                        20                 25                 30

Gly Met Thr Asn Lys Lys Ser Leu Lys Cys Glu Gln His Leu Gly His
                        35                 40                 45

Asn Ala Met Tyr Trp Tyr Lys Gln Ser Ala Lys Lys Pro Leu Glu Leu
                        50                 55                 60

Met Phe Val Tyr Ser Leu Glu Glu Arg Val Glu Asn Asn Ser Val Pro
         65                 70                75                  80

Ser Arg Phe Ser Pro Glu Cys Pro Asn Ser Ser His Leu Phe Leu His
                        85                 90                 95
```

```
Leu His Thr Leu Gln Pro Glu Asp Ser Ala Leu Tyr Leu Cys Ala Ser
            100                 105                 110

Ser Gln Thr Thr Tyr Tyr Asn Glu Gln Phe Phe Gly Pro Gly Thr Arg
            115                 120                 125

Leu Thr Val Leu Glu Asp Leu Lys Asn Val Phe Pro Pro Glu Val Ala
            130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
            195                 200                 205

Ser Ser Arg Leu Arg Val Ser Ala Thr Phe Trp Gln Asn Pro Arg Asn
            210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
            275                 280                 285

Thr Leu Tyr Ala Val Leu Val Ser Ala Leu Val Leu Met Ala Met Val
            290                 295                 300

Lys Arg Lys Asp Ser Arg Gly
305                 310

<210> SEQ ID NO 46
<211> LENGTH: 1827
<212> TYPE: DNA
<213> ORGANISM: Homo sapiens

<400> SEQUENCE: 46
atgatatcct tgagagtttt actggtgatc ctgtggcttc agttaagctg ggtttggagc    60
caacggaagg aggtggagca ggatcctgga cccttcaatg ttccagaggg agccactgtc   120
gctttcaact gtacttacag caacagtgct tctcagtctt tcttctggta cagacaggat   180
tgcaggaaag aacctaagtt gctgatgtcc gtatactcca gtggtaatga agatggaagg   240
tttacagcac agctcaatag agccagccag tatatttccc tgctcatcag agactccaag   300
ctcagtgatt cagccaccta cctctgtgtg gtgaaccgcg acaatgacat gcgctttgga   360
gcagggacca gactgacagt aaaaccaaat atccagaacc ctgaccctgc cgtgtaccag   420
ctgagagact ctaaatccag tgacaagtct gtctgcctat tcaccgatat tgattctcaa   480
acaaatgtgt cacaaagtaa ggattctgat gtgtatatca gacaaaaac tgtgctagac   540 atgaggtcta tggacttcaa gagcaacagt gctgtggcct ggagcaacaa atctgacttt   600
gcatgtgcaa acgccttcaa caacagcatt attccagaag acaccttctt ccccagccca   660
gaaagttcct gtgatgtcaa gctggtcgag aaaagctttg aaacagatac gaacctaaac   720
tttcaaaacc tgtcagtgat tgggttccga atcctcctcc tgaaagtggc cgggtttaat   780
ctgctcatga cgctgcggct gtggtccagc cgggccaagc ggtccggatc cggagccacc   840
aacttcagcc tgctgaagca ggccggcgac gtggaggaga ccccggcccc atggcctcc   900
```

-continued

```
ctgctcttct tctgtgggc cttttatctc ctgggaacag gtccatgga tgctgatgtt      960 acccagaccc caaggaatag gatcacaaag acaggaaaga ggattatgct ggaatgttct   1020
cagactaagg gtcatgatag aatgtactgg tatcgacaag acccaggact gggcctacgg   1080
ttgatctatt actcctttga tgtcaaagat ataaacaaag gagagatctc tgatggatac   1140
agtgtctctc gacaggcaca ggctaaattc tccctgtccc tagagtctgc catccccaac   1200
cagacagctc tttacttctg tgccaccagt gagggagggc cgccctacga gcagtacttc   1260
gggccgggca ccaggctcac ggtcacagag gacctgaaaa acgtgttccc acccgaggtc   1320
gctgtgtttg agccatcaga agcagagatc tcccacaccc aaaaggccac actggtgtgc   1380
ctggccacag gcttctaccc cgaccacgtg gagctgagct ggtgggtgaa tgggaaggag   1440
gtgcacagtg gggtcagcac agacccgcag cccctcaagg agcagcccgc cctcaatgac   1500
tccagatact gcctgagcag ccgcctgagg gtctcggcca ccttctggca gaaccccgc    1560 aaccacttcc gctgtcaagt ccagttctac gggctctcgg agaatgacga gtggaccccag  1620 gatagggcca aacctgtcac ccagatcgtc agcgccgagg cctggggtag agcagactgt   1680 ggcttcaccct ccgagtctta ccagcaaggg gtcctgtctg ccaccatcct ctatgagatc   1740
ttgctaggga aggccacctt gtatgccgtg ctggtcagtg ccctcgtgct gatggcyatg   1800
gtcaagagaa aggattccag aggctag                                        1827
```

<210> SEQ ID NO 47  
<211> LENGTH: 1821  
<212> TYPE: DNA  
<213> ORGANISM: Homo sapiens

<400> SEQUENCE: 47

```
atgacatcca ttcgagctgt atttatattc ctgtggctgc agctggactt ggtgaatgga     60
gagaatgtgg agcagcatcc ttcaaccctg agtgtccagg agggagacag cgctgttatc   120
aagtgtactt attcagacag tgcctcaaac tacttccctt ggtataagca agaacttgga   180
aaaagacctc agcttattat agacattcgt tcaaatgtgg gcgaaaagaa agaccaacga   240
attgctgtta cattgaacaa gacagccaaa catttctccc tgcacatcac agagacccaa   300
cctgaagact cggctgtcta cttctgtgca gcaagtgggg ccaccgacaa gctcatcttt   360
gggactggga ccagattaca agtctttcca aatatccaga accctgaccc tgccgtgtac   420
cagctgagag actctaaatc cagtgacaag tctgtctgcc tattcaccga ttttgattct   480
caaacaaatg tgtcacaaag taaggattct gatgtgtata tcacagacaa aactgtgcta   540
gacatgaggt ctatggactt caagagcaac agtgctgtgg cctggagcaa caaatctgac   600
tttgcatgtg caaacgcctt caacaacagc attattccag aagacacctt cttccccagc   660
ccagaaagtt cctgtgatgt caagctggtc gagaaaagct ttgaaacaga tacgaaccta   720
aactttcaaa acctgtcagt gattgggttc cgaatcctcc tcctgaaagt ggccgggttt   780
aatctgctca tgacgctgcg gctgtggtcc agccgggcca agcggtccgg atccggagcc   840
accaacttca gcctgctgaa gcaggccggc gacgtggagg agaacccccgg ccccatgact   900 atcaggctcc tctgctacat gggcttttat tttctggggg caggcctcat ggaagctgac   960
atctaccaga ccccaagata ccttgttata gggacaggaa agaagatcac tctggaatgt   1020
tctcaaacca tgggccatga caaaatgtac tggtatcaac aagatccagg aatggaacta   1080 caccctcatcc actattccta tggagttaat tccacagaga agggagatct ttcctccgag   1140
```

| | | |
|---|---|---|
| tcaacagtct ccagaataag gacggagcat tttcccctga ccctggagtc tgccaggccc | 1200 | |
| tcacatacct ctcagtacct ctgtgccagc agtggcgggc acgagcagta cttcgggccg | 1260 | |
| ggcaccaggc tcacggtcac agaggacctg aaaaacgtgt tcccacccga ggtcgctgtg | 1320 | |
| tttgagccat cagaagcaga gatctcccac acccaaaagg ccacactggt gtgcctggcc | 1380 | |
| acaggcttct tccctgacca cgtggagctg agctggtggg tgaatgggaa ggaggtgcac | 1440 | |
| agtggggtca gcacggaccc gcagcccctc aaggagcagc ccgccctcaa tgactccaga | 1500 | |
| tactgcctga gcagccgcct gagggtctcg gccaccttct ggcagaaccc ccgcaaccac | 1560 | |
| ttccgctgtc aagtccagtt ctacgggctc tcggagaatg acgagtggac ccaggatagg | 1620 | |
| gccaaacccg tcacccagat cgtcagcgcc gaggcctggg gtagagcaga ctgtggcttt | 1680 | |
| acctcggtgt cctaccagca agggtcctg tctgccacca tcctctatga gatcctgcta | 1740 | |
| gggaaggcca ccctgtatgc tgtgctggtc agcgcccttg tgttgatggc tatggtcaag | 1800 | |
| agaaaggatt ccagaggcta g | 1821 | |

<210> SEQ ID NO 48
<211> LENGTH: 1830
<212> TYPE: DNA
<213> ORGANISM: Homo sapiens

<400> SEQUENCE: 48

| | | |
|---|---|---|
| atgatgaaat ccttgagagt tttactggtg atcctgtggc ttcagttaag ctgggtttgg | 60 | |
| agccaacaga aggaggtgga gcaggatcct ggaccactca gtgttccaga gggagccatt | 120 | |
| gtttctctca actgcactta cagcaacagt gcttttcaat acttcatgtg gtacagacag | 180 | |
| tattccagaa aaggccctga gttgctgatg tacacatact ccagtggtaa caaagaagat | 240 | |
| ggaaggttta cagcacaggt cgataaatcc agcaagtata tctccttgtt catcagagac | 300 | |
| tcacagccca gtgattcagc cacctacctc tgtgcaatgc ggggagccca aagctggta | 360 | |
| tttggccaag gaaccaggct gactatcaac ccaaatatcc agaaccctga ccctgccgtg | 420 | |
| taccagctga gagactctaa atccagtgac aagtctgtct gcctattcac cgattttgat | 480 | |
| tctcaaacaa atgtgtcaca agtaaggat tctgatgtgt atatcacaga caaaactgtg | 540 | |
| ctagacatga ggtctatgga cttcaagagc aacagtgctg tggcctggag caacaaatct | 600 | |
| gactttgcat gtgcaaacgc cttcaacaac agcattattc agaagacac cttcttcccc | 660 | |
| agcccagaaa gttcctgtga tgtcaagctg gtcgagaaaa gctttgaaac agatacgaac | 720 | |
| ctaaactttc aaaacctgtc agtgattggg ttccgaatcc tcctcctgaa agtggccggg | 780 | |
| tttaatctgc tcatgacgct gcggctgtgg tccagacggg ccaagcggtc cggatccgga | 840 | |
| gccaccaact tcagcctgct gaagcaggcc tgcgacgtgg aggagaaccc cggccccatg | 900 | |
| ggtcctgggc ttctccactg gatggccctt gtctccttg aacaggtca tggggatgcc | 960 | |
| atggtcatcc agaacccaag ataccaggtt acccagtttg aaagccagt gaccctgagt | 1020 | |
| tgttctcaga ctttgaacca taacgtcatg tactggtacc agcagaagtc aagtcaggcc | 1080 | |
| ccaaagctgc tgttccacta ctatgacaaa gatttaaca atgaagcaga cacccctgat | 1140 | |
| aacttccaat ccaggaggcc gaacacttct ttctgctttc ttgacatccg ctcaccaggc | 1200 | |
| ctgggggacg cagccatgta cctgtgtgcc acctcctggg accgagggta cgagcagtac | 1260 | |
| ttcgggccgg gcaccaggct cacggtcaca gaggacctga aaacgtgtt cccacccgag | 1320 | |
| gtcgctgtgt ttgagccatc agaagcagag atctcccaca cccaaaaggc cacactggtg | 1380 | |
| tgcctggcca caggcttcta ccccgaccac gtggagctga gctggtgggt gaatgggaag | 1440 | |

| | | |
|---|---|---|
| gaggtgcaca | gtggggtcag cacagacccg cagcccctca aggagcagcc cgccctcaat | 1500 |
| gactccagat | actgcctgag cagccgcctg agggtctcgg ccaccttctg cagaacccc | 1560 |
| cgcaaccact | tccgctgtca agtccagttc tacgggctct cggagaatga cgagtggacc | 1620 |
| caggataggg | ccaaacctgt cacccagatc gtcagcgccg aggcctgggg tagagcagac | 1680 |
| tgtggcttca | cctccgagtc ttaccagcaa ggggtcctgt ctgccaccat cctctatgag | 1740 |
| atcttgctag | ggaaggccac cttgtatgcc gtgctggtca gtgccctcgt gctgatggct | 1800 |
| atggtcaaga | gaaaggattc cagaggctag | 1830 |

<210> SEQ ID NO 49
<211> LENGTH: 1848
<212> TYPE: DNA
<213> ORGANISM: Homo sapiens

<400> SEQUENCE: 49

| | | |
|---|---|---|
| atggcatgcc | ctggcttcct gtgggcactt gtgatctcca cctgtcttga atttagcatg | 60 |
| gctcagacag | tcactcagtc tcaaccagag atgtctgtgc aggaggcaga gaccgtgacc | 120 |
| ctgagctgca | catatgacac cagtgagagt gattattatt tattctggta caagcagcct | 180 |
| cccagcaggc | agatgattct cgttattcgc caagaagctt ataagcaaca gaatgcaaca | 240 |
| gagaatcgtt | tctctgtgaa cttccagaaa gcagccaaat ccttcagtct caagatctca | 300 |
| gactcacagc | tggggggatgc cgcgatgtat ttctgtgctt ataggagcgc tcagggcgga | 360 |
| tctgaaaagc | tggtctttgg aaagggaacg aaactgacag taaacccata tatccagaac | 420 |
| cctgaccctg | ccgtgtacca gctgagagac tctaaatcca gtgacaagtc tgtctgccta | 480 |
| ttcaccgatt | ttgattctca aacaaatgtg tcacaaagta aggattctga tgtgtatatc | 540 |
| acagacaaaa | ctgtgctaga catgaggtct atggacttca gagcaacag tgctgtggcc | 600 |
| tggagcaaca | aatctgactt tgcatgtgca aacgccttca caacagcat tattccagaa | 660 |
| gacaccttct | tccccagccc agaaagttcc tgtgatgtca agctggtcga gaaaagcttt | 720 |
| gaaacagata | cgaacctaaa ctttcaaaac ctgtcagtga ttgggttccg aatcctcctc | 780 |
| ctgaaagtgg | ccgggtttaa tctgctcatg acgctgcggc tgtggtccag ccgggccaag | 840 |
| cggtccggat | ccggagccac caacttcagc ctgctgaagc aggccggcga cgtggaggag | 900 |
| aacccccggcc | ccatgggctg caggctgctc tgctgtgcgg ttctctgtct cctgggagcg | 960 |
| gtccccatgg | aaacgggagt tacgcagaca ccaagacacc tggtcatggg aatgacaaat | 1020 |
| aagaagtctt | tgaaatgtga acaacatctg ggtcataacg ctatgtattg gtacaagcaa | 1080 |
| agtgctaaga | agccactgga gctcatgttt gtctacagtc ttgaagaacg ggttgaaaac | 1140 |
| aacagtgtgc | caagtcgctt ctcaccggaa tgccccaaca gctctcactt attccttcac | 1200 |
| ctacacaccc | tgcagccaga agactcggcc ctgtatctct cgccagcag ccaaactact | 1260 |
| tactacaatg | agcagttctt cggggccaggg acacggctca ccgtgctaga ggacctgaaa | 1320 |
| aacgtgttcc | cacccgaggt cgctgtgttt gagccatcag aagcagagat ctcccacacc | 1380 |
| caaaaggcca | cactggtgtg cctggccaca ggcttctacc ccgaccacgt ggagctgagc | 1440 |
| tggtgggtga | atgggaagga ggtgcacagt ggggtcagca cagacccgca gcccctcaag | 1500 |
| gagcagcccg | ccctcaatga ctccagatac tgcctgagca gccgcctgag ggtctcggcc | 1560 |
| accttctggc | agaaccccg caaccacttc cgctgtcaag tccagttcta cgggctctcg | 1620 |
| gagaatgacg | agtggaccca ggatagggcc aaacccgtca cccagatcgt cagcgccgag | 1680 |

```
gcctggggta gagcagactg tggcttcacc tccgagtctt accagcaagg ggtcctgtct    1740
gccaccatcc tctatgagat cttgctaggg aaggccacct tgtatgccgt gctggtcagt    1800
gccctcgtgc tgatggccat ggtcaagaga aaggattcca gaggctag                 1848
```

<210> SEQ ID NO 50
<211> LENGTH: 9
<212> TYPE: PRT
<213> ORGANISM: Homo sapiens

<400> SEQUENCE: 50

```
Val Pro Ile Ser His Leu Tyr Ile Leu
1               5
```

<210> SEQ ID NO 51
<211> LENGTH: 9
<212> TYPE: PRT
<213> ORGANISM: Homo sapiens

<400> SEQUENCE: 51

```
Asp Pro Ile Gly His Leu Tyr Ile Phe
1               5
```

<210> SEQ ID NO 52
<211> LENGTH: 9
<212> TYPE: PRT
<213> ORGANISM: Homo sapiens

<400> SEQUENCE: 52

```
Asp Pro Ile Gly His Val Tyr Ile Phe
1               5
```

<210> SEQ ID NO 53
<211> LENGTH: 9
<212> TYPE: PRT
<213> ORGANISM: Homo sapiens

<400> SEQUENCE: 53

```
Glu Asp Gly Cys Pro Ala Ala Glu Lys
1               5
```

<210> SEQ ID NO 54
<211> LENGTH: 27
<212> TYPE: PRT
<213> ORGANISM: Artificial Sequence
<220> FEATURE:
<223> OTHER INFORMATION: Synthetic

<400> SEQUENCE: 54

```
Arg Ala Lys Arg Ser Gly Ser Gly Ala Thr Asn Phe Ser Leu Leu Lys
1               5                   10                  15

Gln Ala Cys Asp Val Glu Glu Asn Pro Gly Pro
            20                  25
```

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55

```
cactgttgct cttgaagtcc                                                  20
```

```
<210> SEQ ID NO 56
<211> LENGTH: 24
<212> TYPE: DNA
<213> ORGANISM: Artificial Sequence
<220> FEATURE:
<223> OTHER INFORMATION: Synthetic

<400> SEQUENCE: 56
caggcagtat ctggagtcat tgag                                            24

<210> SEQ ID NO 57
<211> LENGTH: 4
<212> TYPE: PRT
<213> ORGANISM: Artificial Sequence
<220> FEATURE:
<223> OTHER INFORMATION: Synthetic

<400> SEQUENCE: 57

Ser Gly Ser Gly
1

<210> SEQ ID NO 58
<211> LENGTH: 27
<212> TYPE: DNA
<213> ORGANISM: Artificial Sequence
<220> FEATURE:
<223> OTHER INFORMATION: Synthetic

<400> SEQUENCE: 58
tgcaaggcat ggaaaataca taactga                                         27

<210> SEQ ID NO 59
<211> LENGTH: 25
<212> TYPE: DNA
<213> ORGANISM: Artificial Sequence
<220> FEATURE:
<223> OTHER INFORMATION: Synthetic

<400> SEQUENCE: 59
cacagatatc ctgtttggcc catat                                           25

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
tctctctgtt cctaaccttg                                                 20

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
tccgtgagga ggcaaggttc                                                 20

<210> SEQ ID NO 62
<211> LENGTH: 19
<212> TYPE: DNA
<213> ORGANISM: Artificial Sequence
<220> FEATURE:
<223> OTHER INFORMATION: Synthetic
```

```
<400> SEQUENCE: 62
gagcctgcgc acccaccaa                                              19

<210> SEQ ID NO 63
<211> LENGTH: 28
<212> TYPE: DNA
<213> ORGANISM: Artificial Sequence
<220> FEATURE:
<223> OTHER INFORMATION: Synthetic

<400> SEQUENCE: 63
agtgtgggca ggagctagtg ctgctccg                                    28
```

T CELL RECEPTORS RECOGNIZING HLA-A1- OR HLA-CW7-RESTRICTED MAGE

CROSS-REFERENCE TO RELATED APPLICATIONS

This application is a divisional of U.S. application Ser. No. 14/344,354, which is the U.S. national stage of PCT/US2012/054623, filed Sep. 11, 2012, which claims priority to U.S. Application No. 61/535,086, filed Sep. 15, 2011, each of which is incorporated by reference herein in its entirety.

STATEMENT REGARDING FEDERALLY SPONSORED RESEARCH AND DEVELOPMENT

This invention was made with Government support under project number ZIABC010984 by the National Institutes of Health, National Cancer Institute. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 52,252 Byte ASCII (Text) file named "740419 ST25.txt," dated Sep. 27, 2018.

BACKGROUND OF THE INVENTION

Adoptive cell therapy (ACT) involves the transfer of reactive T cells into patients, including the transfer of tumor-reactive T cells into cancer patients. Adoptive cell therapy using T-cells that target human leukocyte antigen (HLA)-A2 restricted T-cell epitopes has been successful in causing the regression of tumors in some patients. However, patients that lack HLA-A2 expression cannot be treated with T-cells that target HLA-A2 restricted T-cell epitopes. Such a limitation creates an obstacle to the widespread application of adoptive cell therapy. Accordingly, there exists a need for improved immunological compositions and methods for treating cancer.

BRIEF SUMMARY OF THE INVENTION

The invention provides an isolated or purified T cell receptor (TCR) having antigenic specificity for a) melanoma antigen family A (MAGE A)-3 in the context of HLA-A1 or b) MAGE-A12 in the context of HLA-Cw7. The invention further provides related polypeptides and proteins, as well as related nucleic acids, recombinant expression vectors, host cells, and populations of cells. Further provided by the invention are antibodies, or antigen binding portions thereof, and pharmaceutical compositions relating to the TCRs of the invention.

Methods of detecting the presence of cancer in a host and methods of treating or preventing cancer in a host are further provided by the invention. The inventive method of detecting the presence of cancer in a host comprises (i) contacting a sample comprising cells of the cancer with any of the inventive TCRs, polypeptides, proteins, nucleic acids, recombinant expression vectors, host cells, populations of host cells, or antibodies, or antigen binding portions thereof, described herein, thereby forming a complex, and (ii) detecting the complex, wherein detection of the complex is indicative of the presence of cancer in the host.

The inventive method of treating or preventing cancer in a host comprises administering to the host any of the TCRs, polypeptides, or proteins described herein, any nucleic acid or recombinant expression vector comprising a nucleotide sequence encoding any of the TCRs, polypeptides, proteins described herein, or any host cell or population of host cells comprising a recombinant vector which encodes any of the TCRs, polypeptides, or proteins described herein, in an amount effective to treat or prevent cancer in the host.

BRIEF DESCRIPTION OF THE SEVERAL VIEWS OF THE DRAWING(S)

FIG. 1A is a bar graph showing interferon (IFN)-γ secretion (pg/ml) of untransduced (UT) cells (black bars) or cells transduced with anti-MAGE-A3 TCR A10 (SEQ ID NO: 46) (unshaded bars) or anti-MAGE-A3 TCR 13-18 (SEQ ID NO: 48) (grey bars) in response to co-culture with various tumor cell lines.

FIG. 1B is a bar graph showing IFN-γ secretion (pg/ml) of UT cells or cells transduced with anti-MAGE-A3 TCR A10 (SEQ ID NO: 46) or anti-MART-1 TCR DMFS in response to co-culture with HLA-A1+/MAGE-A3+ fresh tumors FrTu 2767 (black bars), FrTu 3178 (grey bars), FrTu 2823 (unshaded bars) or FrTu 3068 (diagonal lined bars) or HLA-A*0201+/MART-1+ fresh tumors FrTu 2851 (horizontal lined bars) or FrTu 3242 (vertical lined bar). Checkered bars indicate cells co-cultured with no tumor cells.

FIGS. 2A and 2B are bar graphs showing IFN-γ secretion (pg/ml) of cells from first (FIG. 2A) and second (FIG. 2B) donors transduced with a control construct encoding the truncated human low affinity nerve growth factor receptor (NGFR) (black bars), anti-MAGE-A12 TCR 502 (SEQ ID NO: 47) (unshaded bars), or anti-MAGE-A12 TCR FM8 (SEQ ID NO: 49) (grey bars) in response to co-culture with various tumor cell lines.

FIG. 3A is a bar graph illustrating the cumulative percentage of the normal Caucasian population that expresses HLA-A1 (unshaded portion of bar), HLA-A2 (grey portion of bar), and/or HLA-Cw7 (black portion of bar).

FIGS. 3B and 3C are bar graphs illustrating the cumulative percentage of the human melanoma (FIG. 3B) and synovial cell sarcoma (FIG. 3C) patient populations that would be expected to express HLA-A2 and NY-ESO-1 (diagonal lined portion of bar); HLA-A1 and MAGE-A3 (unshaded portion of bar); HLA-A2, MAGE-A3, and MAGE-A12 (grey portion of bar); and/or HLA-Cw7 and MAGE-A12 (black portion of bar).

FIG. 4 is a bar graph showing IFN-γ secretion (pg/ml) of cells transduced with NGFR (black bars), anti-MAGE-A12 TCR 502 (SEQ ID NO: 47) (unshaded bars), or anti-MAGE-A12 TCR FM8 (SEQ ID NO: 49) (grey bars) in response to co-culture with HLA-Cw*0701 and HLA-Cw*0702 target cells pulsed with peptides from MAGE-A12 (VRIGHLYIL; SEQ ID NO: 4), MAGE-A2 (VPISHLYIL; SEQ ID NO: 50), MAGE-A3 (DPIGHLYIF; SEQ ID NO: 51), MAGE-A6 (DPIGHVYIF; SEQ ID NO: 52), or control peptide (EDGCPAAEK; SEQ ID NO: 53).

FIGS. 5A-5D are line graphs showing percent lysis of 397 mel (A), 624 mel (B), 2984 mel (C), and 2661 RCC (D) cells by PBMC that were untransduced (closed circles) or transduced with anti-MAGE-A12 TCR 502 (SEQ ID NO: 47) (▼), anti-MAGE-A12 TCR FM8 (SEQ ID NO: 49) (diamonds), anti-MAGE-A3 TCR A10 (SEQ ID NO: 46) (squares), anti-MAGE-A3 TCR 13-18 (SEQ ID NO: 48)

(▲), or anti-MAGE-A3 TCR 112-120 (open circles) at the indicated effector to target (E:T) ratios. Representative results from one of two independent experiments are presented.

FIG. 6A is a bar graph showing IFN-γ secretion (pg/ml) of untransduced (control) cells (striped bars) or cells transduced with anti-MAGE-A3 TCR A10 (SEQ ID NO: 46) (shaded bars) or anti-MAGE-A3 TCR 13-18 (SEQ ID NO: 48) (checkered bars) in response to co-culture with various tumor cell lines. Representative results from two of three independent experiments assessing responses of T cells transduced with these TCRs are presented.

Figure 6B:
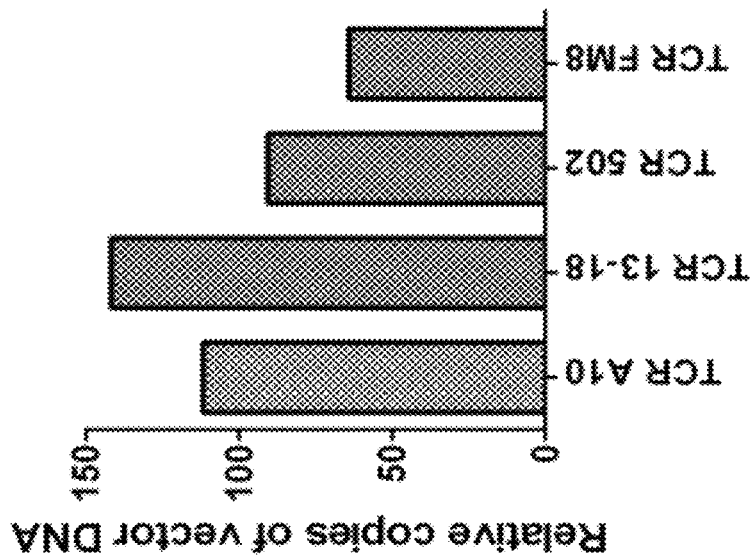
FIG. 6B is a bar graph showing estimated relative copies of vector DNA measured for cells transduced with anti-MAGE-A3 TCR A10 (SEQ ID NO: 46), anti-MAGE-A3 TCR 13-18 (SEQ ID NO: 48), anti-MAGE-A12 TCR 502 (SEQ ID NO: 47), or anti-MAGE-A12 TCR FM8 (SEQ ID NO: 49).
Figure 6A:
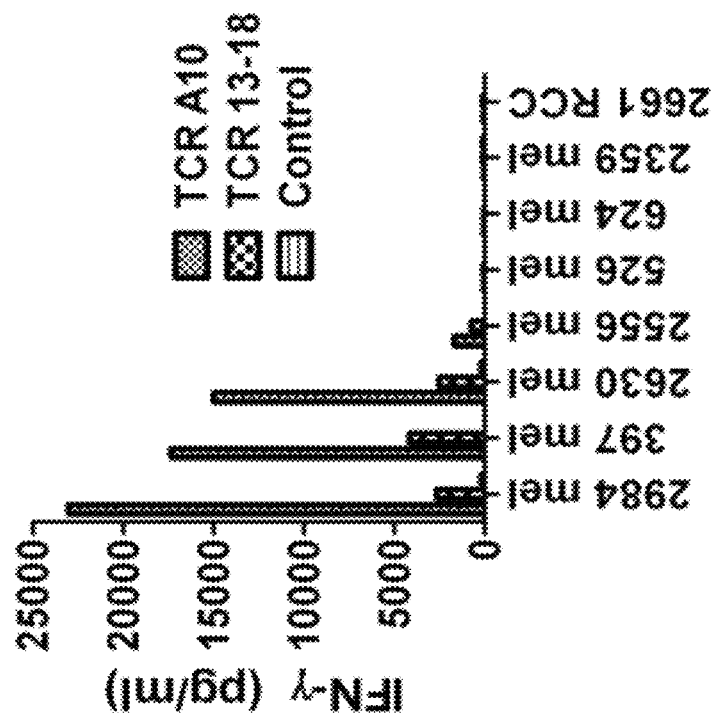
FIG. 6C is a line graph showing the amount of IFN-gamma secreted by cells transduced with anti-MAGE-A3 TCR A10 (SEQ ID NO: 46) (circles) or anti-MAGE-A3 TCR 13-18 (SEQ ID NO: 48) (squares) in response to co-culture with target cells incubated with various concentrations of MAGE-A3 168-176 peptide.
FIG. 6D is a bar graph showing IFN-γ secretion (pg/ml) of cells transduced with anti-MAGE-A12 TCR 502 (SEQ ID NO: 47) (shaded bars) or anti-MAGE-A12 TCR FM8 (SEQ ID NO: 49) (checkered bars) in response to co-culture with various tumor cell lines. Representative results from two of three independent experiments assessing responses of T cells transduced with these TCRs are presented.
FIG. 6E is a line graph showing the amount of IFN-gamma secreted by cells transduced with anti-MAGE-A12 TCR 502 (SEQ ID NO: 47) (circles) or anti-MAGE-A12 TCR FM8 (SEQ ID NO: 49) (squares) in response to co-culture with target cells incubated with various concentrations of MAGE-A12:170-178 peptide.
Figure 6D:
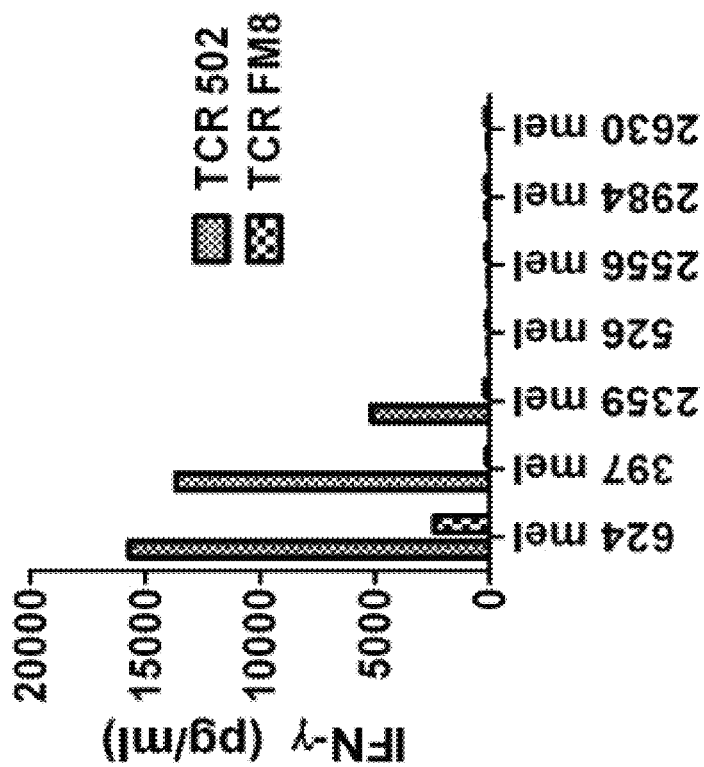
Figure 6C:
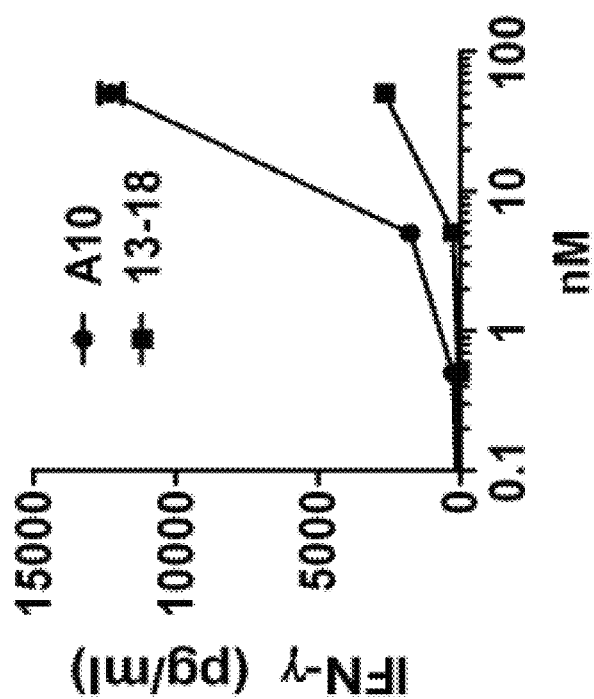
Figure 6F:
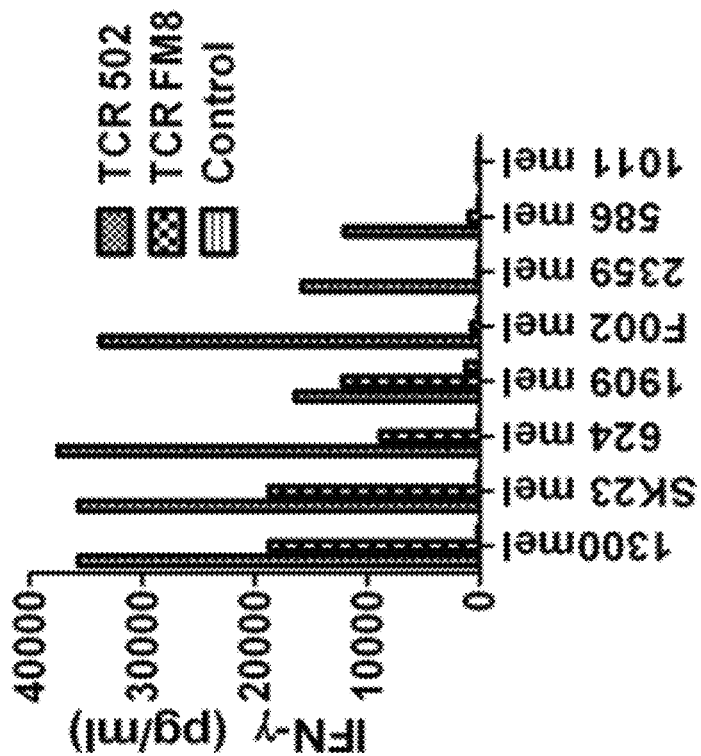

FIG. 6F is a bar graph showing IFN-γ secretion (pg/ml) of cells untransduced (control) (striped bars) or transduced with anti-MAGE-A12 TCR 502 (SEQ ID NO: 47) (shaded bars) or anti-MAGE-A12 TCR FM8 (SEQ ID NO: 49) (checkered bars) in response to co-culture with various tumor cell lines. Representative results from two of three independent experiments assessing responses of T cells transduced with these TCRs are presented.

Figure 7B:
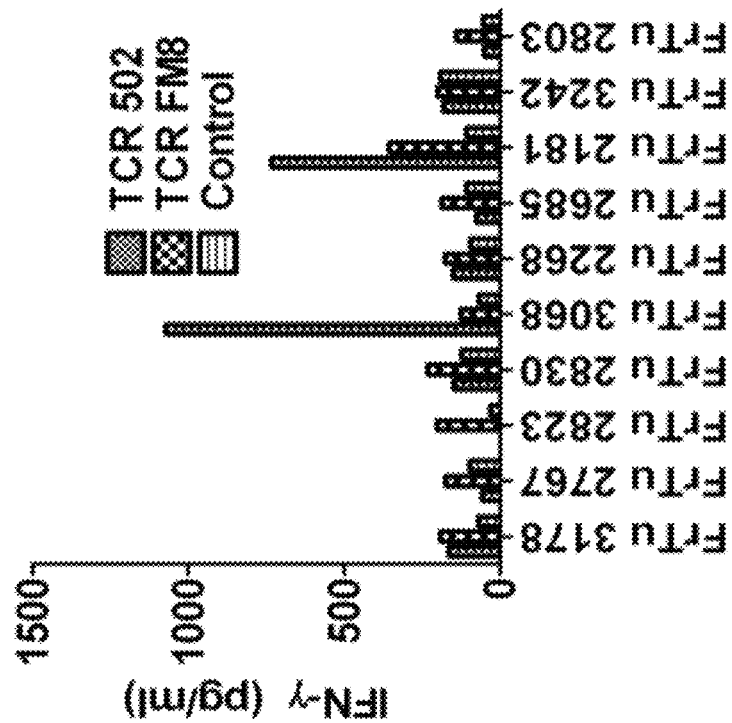
Figure 7A:
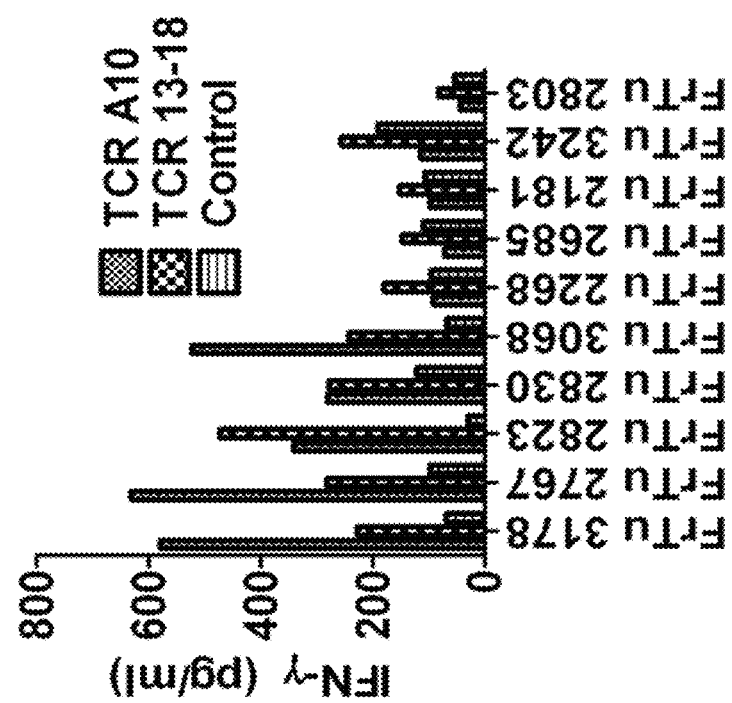

FIG. 7A is a bar graph showing IFN-γ secretion (pg/ml) of untransduced cells (control) (striped bars) or cells transduced with anti-MAGE-A3 TCR A10 (SEQ ID NO: 46) (shaded bars) or anti-MAGE-A3 TCR 13-18 (checkered bars) in response to co-culture with various fresh uncultured tumors. Representative results from one of three independent experiments assessing responses of T cells transduced with these TCRs are presented.

FIG. 7B is a bar graph showing IFN-γ secretion (pg/ml) of untransduced cells (control) (striped bars) or cells transduced with anti-MAGE-A12 TCR 502 (SEQ ID NO: 47) (shaded bars) or anti-MAGE-A12 TCR FM8 (SEQ ID NO: 49) (checkered bars) in response to co-culture with various fresh uncultured tumors. Representative results from one of three independent experiments assessing responses of T cells transduced with these TCRs are presented.

Figure 8C:
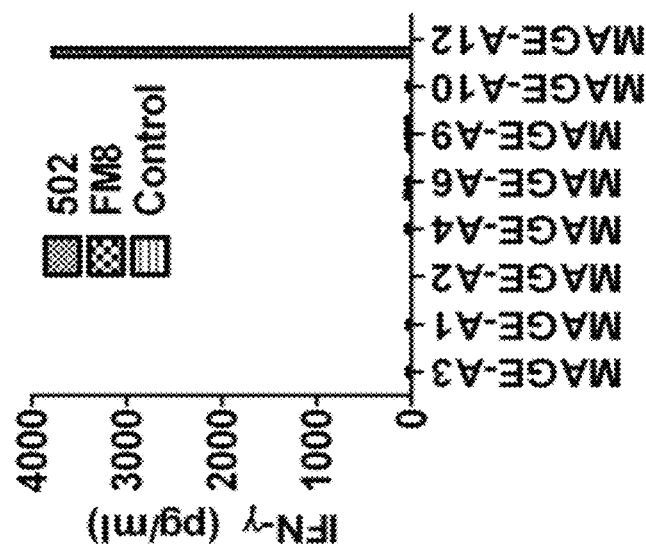
Figure 8B:
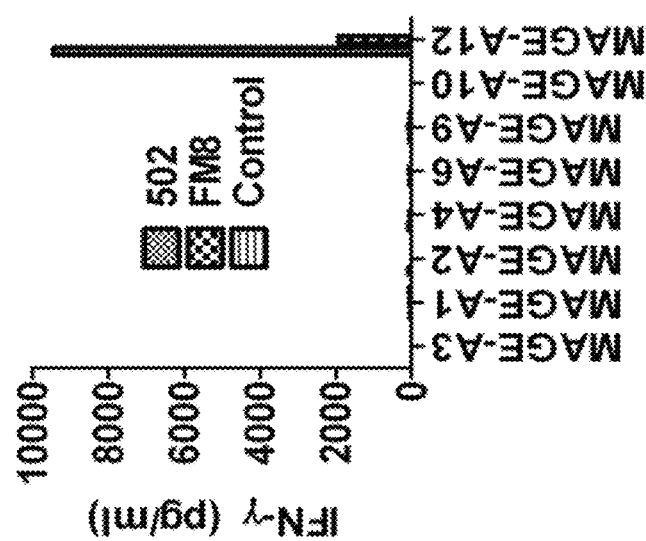
Figure 8A:
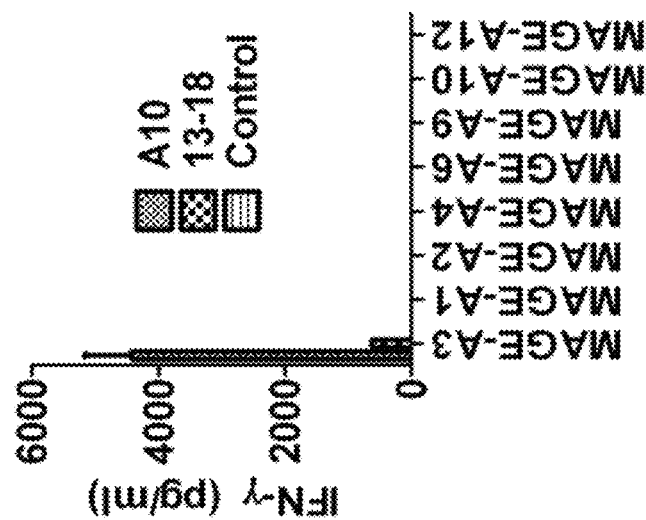

FIG. 8A is a bar graph showing IFN-γ secretion (pg/ml) of untransduced cells (control) (striped bars) or cells transduced with anti-MAGE-A3 TCR A10 (SEQ ID NO: 46) (shaded bars) or anti-MAGE-A3 TCR 13-18 (checkered bars) co-cultured with target cells transfected with HLA-A*01 plus either MAGE-A3, A1, A2, A4, A6, A9, A10 or A12 overnight.

FIG. 8B is a bar graph showing IFN-γ secretion (pg/ml) of untransduced cells (control) (striped bars) or cells transduced with anti-MAGE-A12 TCR 502 (SEQ ID NO: 47) (shaded bars) or anti-MAGE-A12 TCR FM8 (SEQ ID NO: 49) (checkered bars) co-cultured with target cells transfected with HLA-C*07:02 plus either MAGE-A3, A1, A2, A4, A6, A9, A10 or A12 overnight.

FIG. 8C is a bar graph showing IFN-γ secretion (pg/ml) of untransduced cells (control) (striped bars) or cells transduced with anti-MAGE-A12 TCR 502 (SEQ ID NO: 47) (shaded bars) or anti-MAGE-A12 TCR FM8 (SEQ ID NO: 49) (checkered bars) co-cultured with target cells transfected with HLA-C*07:01 plus either MAGE-A3, A1, A2, A4, A6, A9, A10 or A12 overnight.

Figure 9C:
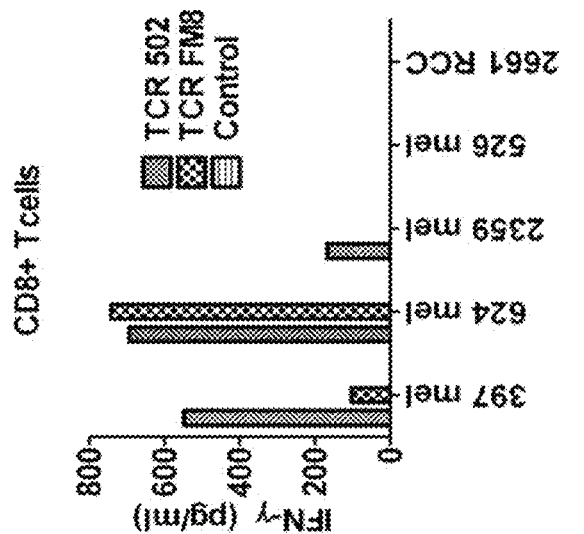
Figure 9B:
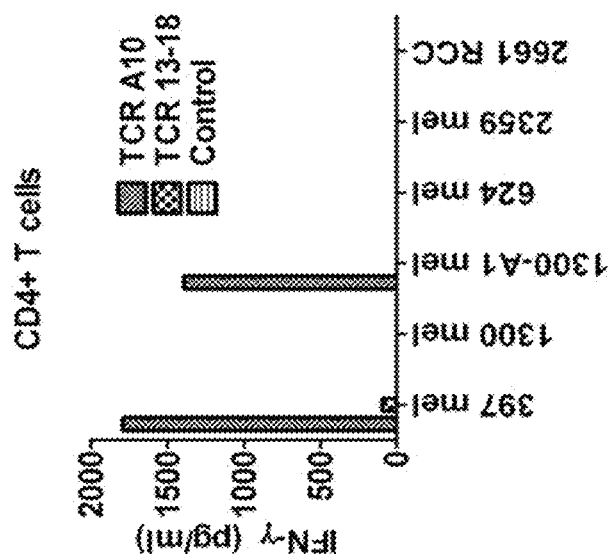
Figure 9A:
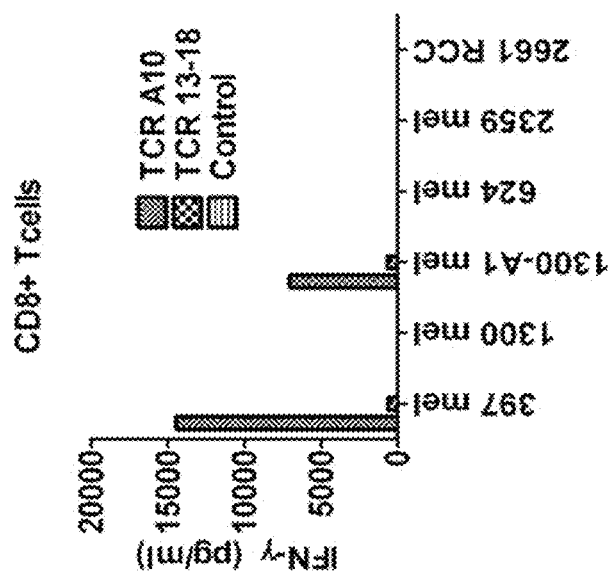

FIGS. 9A and 9B are bar graphs showing IFN-gamma secretion of CD8+ (FIG. 9A) or CD4+ cells (FIG. 9B) that were untransduced (control) (striped bars) or cells transduced with anti-MAGE-A3 TCR A10 (SEQ ID NO: 46) (shaded bars) or anti-MAGE-A3 TCR 13-18 (checkered bars) co-cultured with various tumor targets. Representative results from one of two independent experiments are presented.

FIG. 9C is a bar graph showing IFN-gamma secretion of CD8+ cells that were untransduced (control) (striped bars) or cells transduced with anti-MAGE-A12 TCR 502 (SEQ ID NO: 47) (shaded bars) or anti-MAGE-A12 TCR FM8 (SEQ ID NO: 49) (checkered bars) co-cultured with various tumor targets. Representative results from one of two independent experiments are presented.

DETAILED DESCRIPTION OF THE INVENTION

An embodiment of the invention provides a T cell receptor (TCR) having antigenic specificity for a) melanoma antigen family A (MAGE A)-3 (also known as MAGE-3) in the context of HLA-A1 orb) MAGE-A12 (also known as MAGE-12) in the context of HLA-Cw7.

MAGE-A3 and MAGE-A12 are members of the MAGE-A family of twelve homologous proteins also including MAGE-A1, MAGE-A2, MAGE-A4, MAGE-A5, MAGE-A6, MAGE-A7, MAGE-A8, MAGE-A9, MAGE-A10, and MAGE-A11. The MAGE-A proteins are cancer testis antigens (CTA), which are expressed only in tumor cells and non-MHC expressing germ cells of the testis and placenta. MAGE-A proteins are expressed in a variety of human cancers including, but not limited to, melanoma, breast cancer, leukemia, thyroid cancer, gastric cancer, pancreatic cancer, liver cancer (e.g., hepatocellular carcinoma), lung cancer (e.g., non-small cell lung carcinoma), ovarian cancer, multiple myeloma, esophageal cancer, kidney cancer, head cancers (e.g., squamous cell carcinoma), neck cancers (e.g., squamous cell carcinoma), prostate cancer, and urothelial cancer.

The TCRs of the invention provide many advantages, including when used for adoptive cell transfer. For example, by targeting a) MAGE-A3 that is presented in the context of HLA-A1 or b) MAGE-A12 that is presented in the context of HLA-Cw7, the inventive TCRs make it possible to treat patients who are unable to be treated using TCRs that target MAGE antigens that are presented in the context of other HLA molecules, e.g., HLA-A2. Because HLA-A1 and HLA-Cw7 are highly prevalent alleles, the inventive TCRs advantageously greatly expand the patient population that can be treated. Additionally, without being bound by a particular theory, it is believed that because MAGE-A3 and/or MAGE-A12 are expressed by cells of multiple cancer types, the inventive TCRs advantageously provide the ability to destroy cells of multiple types of cancer and, accordingly, treat or prevent multiple types of cancer. Additionally, without being bound to a particular theory, it is believed that because the MAGE-A proteins are cancer testis antigens that are expressed only in tumor cells and non-MHC expressing germ cells of the testis and placenta, the inventive TCRs advantageously target the destruction of cancer cells while minimizing or eliminating the destruction of normal, non-cancerous cells, thereby reducing, for example, by minimizing or eliminating, toxicity.

The phrase "antigenic specificity" as used herein means that the TCR can specifically bind to and immunologically recognize MAGE-A3 or MAGE-A12 with high avidity. For example, a TCR may be considered to have "antigenic specificity" for MAGE-A3 or MAGE-A12 if T cells expressing the TCR secrete at least about 200 pg/mi or more (e.g., 200 pg/ml or more, 300 pg/ml or more, 400 pg/ml or more, 500 pg/ml or more, 600 pg/ml or more, 700 pg/ml or more, 1000 pg/ml or more, 5,000 pg/ml or more, 7,000 pg/ml or more, 10,000 pg/ml or more) of IFN-γ upon co-culture with antigen-negative HLA-A1+ target cells or HLA-Cw7+ target cells, respectively, pulsed with a low concentration of MAGE-A3 peptide or MAGE-A12 peptide, respectively (e.g., about 0.05 ng/ml to about 5 ng/ml, 0.05 ng/ml, 0.1 ng/ml, 0.5 ng/ml, 1 ng/ml, or 5 ng/ml). Alternatively or additionally, a TCR may be considered to have "antigenic specificity" for MAGE-A3 or MAGE-A12 if T cells expressing the TCR secrete at least twice as much IFN-γ as the untransduced PBL background level of IFN-γ upon co-culture with antigen-negative HLA-A1+ target cells or HLA-Cw7+ target cells, respectively, pulsed with a low concentration of MAGE-A3 peptide or MAGE-A12 peptide, respectively. The inventive TCRs may also secrete IFN-γ upon co-culture with antigen-negative HLA-A1+target cells or HLA-Cw7+ target cells pulsed with higher concentrations of MAGE-A3 peptide or MAGE-A12 peptide, respectively.

An embodiment of the invention provides a TCR with antigenic specificity for any MAGE-A3 protein, polypeptide or peptide. The inventive TCR may have antigenic specificity for a MAGE-A3 protein comprising, consisting of, or consisting essentially of, SEQ ID NO: 1. In a preferred embodiment of the invention, the TCR has antigenic specificity for a MAGE-A3 168-176 peptide comprising, consisting of, or consisting essentially of, EVDPIGHLY (SEQ ID NO: 2).

The inventive TCRs are able to recognize MAGE-A3 in a human leukocyte antigen (HLA)-A1-dependent manner. By "HLA-A1-dependent manner" as used herein means that the TCR elicits an immune response upon binding to a MAGE-A3 cancer antigen within the context of an HLA-A1 molecule. The inventive TCRs are able to recognize MAGE-A3 that is presented by an HLA-A1 molecule and may bind to the HLA-A1 molecule in addition to MAGE-A3. Exemplary HLA-A1 molecules, in the context of which the inventive TCRs recognize MAGE-A3, include those encoded by the HLA-A*0101, HLA-A*0102, and/or HLA-A*0103 alleles.

An embodiment of the invention provides a TCR with antigenic specificity for any MAGE-A12 protein, polypeptide or peptide. The inventive TCR may have antigenic specificity for a MAGE-A12 protein comprising, consisting of, or consisting essentially of, SEQ ID NO: 3. In a preferred embodiment of the invention, the TCR has antigenic specificity for a MAGE-A12 170-178 peptide comprising, consisting of, or consisting essentially of, VRIGHLYIL (SEQ ID NO: 4).

The inventive TCRs are able to recognize MAGE-A12 in an HLA-Cw7-dependent manner. By "HLA-Cw7-dependent manner" as used herein means that the TCR elicits an immune response upon binding to a MAGE-A12 cancer antigen within the context of an HLA-Cw7 molecule. The inventive TCRs are able to recognize MAGE-A12 that is presented by an HLA-Cw7 molecule and may bind to the HLA-Cw7 molecule in addition to MAGE-A12. Exemplary HLA-Cw7 molecules, in the context of which the inventive TCRs recognize MAGE-A12, include those encoded by the HLA-Cw*0701 and/or HLA-Cw*0702 alleles.

The invention provides a TCR comprising two polypeptides (i.e., polypeptide chains), such as an alpha (α) chain of a TCR, a beta (β) chain of a TCR, a gamma (γ) chain of a TCR, a delta (δ) chain of a TCR, or a combination thereof. Such polypeptide chains of TCRs are known in the art. The polypeptides of the inventive TCR can comprise any amino acid sequence, provided that the TCR has antigenic specificity for a) MAGE-A3 in the context of HLA-A1 orb) MAGE-A12 in the context of HLA-Cw7.

In an embodiment of the invention, the TCR comprises two polypeptide chains, each of which comprises a variable region comprising a complementarity determining region (CDR) 1, a CDR2, and a CDR3 of a TCR. In an embodiment of the invention, the TCR has antigenic specificity for MAGE-A3 168-176 and comprises a first polypeptide chain comprising a CDR1 comprising the amino acid sequence of SEQ ID NO: 5 or 16 (CDR1 of α chain), a CDR2 comprising the amino acid sequence of SEQ ID NO: 6 or 17 (CDR2 of α chain), and a CDR3 comprising the amino acid sequence of SEQ ID NO: 7 or 18 (CDR3 of α chain), and a second polypeptide chain comprising a CDR1 comprising the amino acid sequence of SEQ ID NO: 8 or 19 (CDR1 of β chain), a CDR2 comprising the amino acid sequence of SEQ ID NO: 9 or 20 (CDR2 of β chain), and a CDR3 comprising the amino acid sequence of SEQ ID NO: 10 or 21 (CDR3 of β chain). In another embodiment of the invention, the TCR has antigenic specificity for MAGE-A12 170-178, and comprises a first polypeptide chain comprising a CDR1 comprising the amino acid sequence of SEQ ID NO: 26 or 36 (CDR1 of α chain), a CDR2 comprising the amino acid sequence of SEQ ID NO: 27 or 37 (CDR2 of α chain), and a CDR3 comprising the amino acid sequence of SEQ ID NO: 28 or 38 (CDR3 of α chain), and a second polypeptide chain comprising a CDR1 comprising the amino acid sequence of SEQ ID NO: 29 or 39 (CDR1 of β chain), a CDR2 comprising the amino acid sequence of SEQ ID NO: 30 or 40 (CDR2 of β chain), and a CDR3 comprising the amino acid sequence of SEQ ID NO: 31 or 41 (CDR3 of β chain). In this regard, the inventive TCR can comprise any one or more of the amino acid sequences selected from the group consisting of any one or more of SEQ ID NOs: 5-7, 8-10, 16-18, 19-21, 26-28, 29-31, 36-38, and 39-41. Preferably the TCR comprises the amino acid sequences of SEQ ID NOs: 5-10, 16-21, 26-31, or 36-41. More preferably the TCR comprises the amino acid sequences of SEQ ID NOs: 5-10 or 26-31.

Alternatively or additionally, the TCR can comprise an amino acid sequence of a variable region of a TCR comprising the CDRs set forth above. In this regard, the TCR with antigenic specificity for MAGE-A3 168-176 can comprise the amino acid sequence of SEQ ID NO: 11 or 22 (the variable region of an α chain) or 12 or 23 (the variable region of a β chain), both SEQ ID NOs: 11 and 12 or both SEQ ID NOs: 22 and 23. In another embodiment of the invention, the TCR has antigenic specificity for MAGE-A12 170-178 and comprises the amino acid sequence of SEQ ID NO: 32 or 42 (the variable region of an α chain) or 33 or 43 (the variable region of a β chain), both SEQ ID NOs: 32 and 33, or both SEQ ID NOs: 42 and 43. Preferably, the inventive TCR comprises the amino acid sequences of both SEQ ID NOs: 11 and 12 or both SEQ ID NOs: 32 and 33.

Alternatively or additionally, the TCR can comprise an α chain of a TCR and a β chain of a TCR. Each of the α chain and β chain of the inventive TCR can independently comprise any amino acid sequence. Preferably, the α chain comprises the variable region of an α chain as set forth above. In this regard, the inventive TCR with antigenic specificity for MAGE-A3 168-176 can comprise the amino acid sequence of SEQ ID NO: 13 or 24 and the inventive TCR with antigenic specificity for MAGE-A12 170-178 can comprise the amino acid sequence of SEQ ID NO: 34 or 44. An inventive TCR of this type can be paired with any β chain of a TCR. Preferably, the β chain of the inventive TCR comprises the variable region of a β chain as set forth above. In this regard, the inventive TCR with antigenic specificity for MAGE-A3 168-176 can comprise the amino acid sequence of SEQ ID NO: 14 or 25 and the inventive TCR with antigenic specificity for MAGE-A12 170-178 can comprise the amino acid sequence of SEQ ID NO: 35 or 45. The inventive TCR, therefore, can comprise the amino acid sequence of SEQ ID NO: 13, 14, 24, 25, 34, 35, 44, or 45, both SEQ ID NOs: 13 and 14, both SEQ ID NOs: 24 and 25, both SEQ ID NOs: 34 and 35, or both SEQ ID NOs: 44 and 45. Preferably, the inventive TCR comprises the amino acid sequences of both SEQ ID NOs: 13 and 14 or both SEQ ID NOs: 34 and 35.

Also provided by the invention is a polypeptide comprising a functional portion of any of the TCRs described herein. The term "polypeptide" as used herein includes oligopeptides and refers to a single chain of amino acids connected by one or more peptide bonds.

With respect to the inventive polypeptides, the functional portion can be any portion comprising contiguous amino acids of the TCR of which it is a part, provided that the functional portion specifically binds to MAGE-A3 or MAGE-A12. The term "functional portion" when used in reference to a TCR refers to any part or fragment of the TCR of the invention, which part or fragment retains the biological activity of the TCR of which it is a part (the parent TCR). Functional portions encompass, for example, those parts of a TCR that retain the ability to specifically bind to MAGE-A3 (e.g., in an HLA-A1-dependent manner) or MAGE-A12 (e.g., in an HLA-Cw7-dependent manner), or detect, treat, or prevent cancer, to a similar extent, the same extent, or to a higher extent, as the parent TCR. In reference to the parent TCR, the functional portion can comprise, for instance, about 10%, 25%, 30%, 50%, 68%, 80%, 90%, 95%, or more, of the parent TCR.

The functional portion can comprise additional amino acids at the amino or carboxy terminus of the portion, or at both termini, which additional amino acids are not found in the amino acid sequence of the parent TCR. Desirably, the additional amino acids do not interfere with the biological function of the functional portion, e.g., specifically binding to MAGE-A3 or MAGE-A12; and/or having the ability to detect cancer, treat or prevent cancer, etc. More desirably, the additional amino acids enhance the biological activity, as compared to the biological activity of the parent TCR.

The polypeptide can comprise a functional portion of either or both of the α and β chains of the TCRs of the invention, such as a functional portion comprising one of more of CDR1, CDR2, and CDR3 of the variable region(s) of the α chain and/or β chain of a TCR of the invention. In this regard, the polypeptide can comprise a functional portion comprising the amino acid sequence of SEQ ID NO: 5, 16, 26, or 36 (CDR1 of α chain), 6, 17, 27, or 37 (CDR2 of α chain), 7, 18, 28, or 38 (CDR3 of α chain), 8, 19, 29, or 39 (CDR1 of β chain), 9, 20, 30, or 40 (CDR2 of β chain), 10, 21, 31, or 41 (CDR3 of β chain), or a combination thereof. Preferably, the inventive polypeptide comprises a functional portion comprising SEQ ID NOs: 5-7; 8-10; 16-18; 19-21; 26-28; 29-31; 36-38; 39-41; all of SEQ ID NOs: 5-10; all of SEQ ID NOs: 16-21; all of SEQ ID NOs: 26-31; or all of SEQ ID NOs: 36-41. More preferably, the polypeptide comprises a functional portion comprising the amino acid sequences of all of SEQ ID NOs: 5-10 or all of SEQ ID NOs: 26-31.

Alternatively or additionally, the inventive polypeptide can comprise, for instance, the variable region of the inventive TCR comprising a combination of the CDR regions set forth above. In this regard, the polypeptide can comprise the amino acid sequence of SEQ ID NO: 11, 22, 32, or 42 (the variable region of an α chain), SEQ ID NO: 12, 23, 33, or 43 (the variable region of a β chain), both SEQ ID NOs: 11 and 12, both SEQ ID NOs: 22 and 23, both SEQ ID NOs: 32 and 33, or both SEQ ID NOs: 42 and 43. Preferably, the polypeptide comprises the amino acid sequences of both SEQ ID NOs: 11 and 12 or both SEQ ID NOs: 32 and 33.

Alternatively or additionally, the inventive polypeptide can comprise the entire length of an α or β chain of one of the TCRs described herein. In this regard, the inventive polypeptide can comprise an amino acid sequence of SEQ ID NOs: 13, 14, 24, 25, 34, 35, 44, or 45. Alternatively, the polypeptide of the invention can comprise α and β chains of the TCRs described herein. For example, the inventive polypeptide can comprise the amino acid sequences of both SEQ ID NOs: 13 and 14; both SEQ ID NOs: 24 and 25; both SEQ ID NOs: 34 and 35; or both SEQ ID NOs: 44 and 45. Preferably, the polypeptide comprises the amino acid sequences of both SEQ ID NOs: 13 and 14 or both SEQ ID NOs: 34 and 35.

The invention further provides a protein comprising at least one of the polypeptides described herein. By "protein" is meant a molecule comprising one or more polypeptide chains.

In an embodiment, the protein of the invention can comprise a first polypeptide chain comprising the amino acid sequences of SEQ ID NOs: 5-7; SEQ ID NOs: 16-18; SEQ ID NOs: 26-28; or SEQ ID NOs: 36-38 and a second polypeptide chain comprising the amino acid sequence of SEQ ID NOs: 8-10; SEQ ID NOs: 19-21; SEQ ID NOs: 29-31; or SEQ ID NOs: 39-41. Alternatively or additionally, the protein of the invention can comprise a first polypeptide chain comprising the amino acid sequence of SEQ ID NO: 11, 22, 32, or 42 and a second polypeptide chain comprising the amino acid sequence of SEQ ID NO: 12, 23, 33, or 43. The protein of the invention can, for example, comprise a first polypeptide chain comprising the amino acid sequence of SEQ ID NO: 13, 24, 34, or 44 and a second polypeptide chain comprising the amino acid sequence of SEQ ID NO: 14, 25, 35, or 45. In this instance, the protein of the invention can be a TCR. Alternatively, if, for example, the protein comprises a single polypeptide chain comprising SEQ ID NO: 13, 24, 34, or 44 and SEQ ID NO: 14, 25, 35, or 45, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. See, for instance, Choi et al., *Mol. Biotechnol.* 31: 193-202 (2005).

In some embodiments of the invention, the TCRs, polypeptides, and proteins of the invention may be expressed as a single protein comprising a linker peptide linking the α chain and the β chain. In this regard, the TCRs, polypeptides, and proteins of the invention comprising SEQ ID NO: 13, 24, 34, or 44 and SEQ ID NO: 14, 25, 35, or 45 may further comprise a linker peptide comprising SEQ ID NO: 15 or 54. The linker peptide may advantageously facilitate the expression of a recombinant TCR, polypeptide, and/or protein in a host cell. Upon expression of the construct including the linker peptide by a host cell, the linker peptide may be cleaved, resulting in separated α and β chains.

The protein of the invention can be a recombinant antibody comprising at least one of the inventive polypeptides described herein. As used herein, "recombinant antibody" refers to a recombinant (e.g., genetically engineered) protein comprising at least one of the polypeptides of the invention and a polypeptide chain of an antibody, or a portion thereof. The polypeptide of an antibody, or portion thereof, can be a heavy chain, a light chain, a variable or constant region of a heavy or light chain, a single chain variable fragment (scFv), or an Fc, Fab, or F(ab)$_2$' fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide of the invention. The polypeptide of an antibody, or portion thereof, can be a polypeptide of any antibody or any antibody fragment, including any of the antibodies and antibody fragments described herein.

Included in the scope of the invention are functional variants of the inventive TCRs, polypeptides, and proteins described herein. The term "functional variant" as used herein refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to MAGE-A3 or MAGE-A12 for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, 50%, 75%, 80%, 90%, 95%, 96%, 97%, 98%, 99% or more identical in amino acid sequence to the parent TCR, polypeptide, or protein.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

The TCR, polypeptide, or protein can consist essentially of the specified amino acid sequence or sequences described herein, such that other components of the functional variant, e.g., other amino acids, do not materially change the biological activity of the functional variant. In this regard, the inventive TCR, polypeptide, or protein can, for example, consist essentially of the amino acid sequence of SEQ ID NO: 13, 14, 24, 25, 34, 35, 44, or 45, both SEQ ID NOs: 13 and 14, both SEQ ID NOs: 24 and 25, both SEQ ID NOs: 34 and 35, or both SEQ ID NOs: 44 and 45. Also, for instance, the inventive TCRs, polypeptides, or proteins can consist essentially of the amino acid sequence(s) of SEQ ID NO: 11, 12, 22, 23, 32, 33, 42, or 43, both SEQ ID NOs: 11 and 12, both SEQ ID NOs: 22 and 23, both SEQ ID NOs: 32 and 33, or both SEQ ID NOs: 42 and 43. Furthermore, the inventive TCRs, polypeptides, or proteins can consist essentially of the amino acid sequence of SEQ ID NO: 5, 16, 26, or 36 (CDR1 of α chain), SEQ ID NO: 6, 17, 27, or 37 (CDR2 of α chain), SEQ ID NO: 7, 18, 28, or 38 (CDR3 of α chain), SEQ ID NO: 8, 19, 29, or 39 (CDR1 of β chain), SEQ ID NO: 9, 20, 30, or 40 (CDR2 of β chain), SEQ ID NO: 10, 21, 31, or 41 (CDR3 of β chain), or any combination thereof, e.g., SEQ ID NOs: 5-7; 8-10; 5-10; 16-18; 19-21; 16-21; 26-28; 29-31; 26-31; 36-38; 39-41; or 36-41.

The TCRs, polypeptides, and proteins of the invention (including functional portions and functional variants) can be of any length, i.e., can comprise any number of amino acids, provided that the TCRs, polypeptides, or proteins (or functional portions or functional variants thereof) retain their biological activity, e.g., the ability to specifically bind to MAGE-A3 or MAGE-A12; detect cancer in a host; or treat or prevent cancer in a host, etc. For example, the polypeptide can be in the range of from about 50 to about 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention (including functional portions and functional variants) of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

When the TCRs, polypeptides, and proteins of the invention (including functional portions and functional variants) are in the form of a salt, preferably, the polypeptides are in the form of a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The TCR, polypeptide, and/or protein of the invention (including functional portions and functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; and U.S. Pat. No. 5,449,752. Also, polypeptides and proteins can be recombinantly produced using the nucleic acids described herein using standard recombinant methods. See, for instance, Sambrook et al., *Molecular Cloning: A Laboratory Manual*, $3^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994. Further, some of the TCRs, polypeptides, and proteins of the invention (including functional portions and functional variants thereof) can be isolated and/or purified from a source, such as a plant, a bacterium, an insect, a mammal, e.g., a rat, a human, etc. Methods of isolation and purification are well-known in the art. Alternatively, the TCRs, polypeptides, and/or proteins described herein (including functional portions and functional variants thereof) can be commercially synthesized by companies, such as Synpep (Dublin, Calif.), Peptide Technologies Corp. (Gaithersburg, Md.), and Multiple Peptide Systems (San Diego, Calif.). In this respect, the inventive TCRs, polypeptides, and proteins can be synthetic, recombinant, isolated, and/or purified.

Included in the scope of the invention are conjugates, e.g., bioconjugates, comprising any of the inventive TCRs, polypeptides, or proteins (including any of the functional portions or variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-gal actosylqueosine, inosine, $N^6$-isopentenyladenine, 1-methyl guanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, Colo.) and Synthegen (Houston, Tex.).

The nucleic acid can comprise any nucleotide sequence which encodes any of the TCRs, polypeptides, or proteins, or functional portions or functional variants thereof described herein. For example, the nucleic acid can comprise, consist, or consist essentially of any one or more of the nucleotide sequence SEQ ID NOs: 46-49.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs. It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

The nucleic acids of the invention can be incorporated into a recombinant expression vector. In this regard, the invention provides recombinant expression vectors comprising any of the nucleic acids of the invention. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector.

The recombinant expression vectors of the invention can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColEl, 2µ plasmid, X, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein (including functional portions and functional variants thereof), or to the nucleotide sequence which is complementary to or which hybridizes to the nucleotide sequence encoding the TCR, polypeptide, or protein. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression. Further, the recombinant expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, $CD4^+$/$CD8^+$ double positive T cells, $CD4^+$ helper T cells, e.g., $Th_1$ and $Th_2$ cells, $CD8^+$ T cells (e.g., cytotoxic T cells), tumor infiltrating lymphocytes (TILs), memory T cells (e.g., central memory T cells and effector memory T cells), naïve T cells, and the like. Preferably, the T cell is a $CD8^+$ T cell or a $CD4^+$ T cell.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

The invention further provides an antibody, or antigen binding portion thereof, which specifically binds to a functional portion of any of the TCRs described herein. Preferably, the functional portion specifically binds to the cancer antigen, e.g., the functional portion comprising the amino acid sequence SEQ ID NO: 5, 16, 26, or 36 (CDR1 of α chain), 6, 17, 27, or 37 (CDR2 of α chain), 7, 18, 28, or 38 (CDR3 of α chain), 8, 19, 29, or 39 (CDR1 of β chain), 9, 20, 30, or 40 (CDR2 of β chain), 10, 21, 31, or 41 (CDR3 of β chain), SEQ ID NO: 11, 22, 32, or 42 (variable region of α chain), SEQ ID NO: 12, 23, 33, or 43 (variable region of β chain), or a combination thereof, e.g., 5-7; 8-10; 5-10; 16-18, 19-21; 16-21; 26-28; 29-31; 26-31; 36-38; 39-41; or 36-41. More preferably, the functional portion comprises the amino acid sequences of SEQ ID NOs: 5-10 or SEQ ID NOs: 26-31. In a preferred embodiment, the antibody, or antigen binding portion thereof, binds to an epitope which is formed by all 6 CDRs (CDR1-3 of the alpha chain and CDR1-3 of the beta chain). The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive TCR. Desirably, the antibody is specific for the functional portion of the inventive TCR, such that there is minimal cross-reaction with other peptides or proteins.

Methods of testing antibodies for the ability to bind to any functional portion of the inventive TCR are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 5th Ed., Garland Publishing, New York, N.Y. (2001)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1.

Phage display furthermore can be used to generate the antibody of the invention. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual*, 3$^{rd}$ Edition, Cold Spring Harbor Laboratory Press, New York (2001)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in, for example, U.S. Pat. No. 5,639,641 and Pedersen et al., J. Mol. Biol., 235, 959-973 (1994).

The invention also provides antigen binding portions of any of the antibodies described herein. The antigen binding portion can be any portion that has at least one antigen binding site, such as Fab, F(ab')$_2$, dsFv, sFv, diabodies, and triabodies.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering*, 7, 697-704 (1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The inventive TCRs, polypeptides, proteins, (including functional portions and functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70%, 80%, 90%, 95%, or can be 100%.

The inventive TCRs, polypeptides, proteins (including functional portions and variants thereof), nucleic acids, recombinant expression vectors, host cells (including populations thereof), and antibodies (including antigen binding portions thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, functional portions, functional variants, nucleic acids, expression vectors, host cells (including populations thereof), and antibodies (including antigen binding portions thereof), and a pharmaceutically acceptable carrier. The inventive pharmaceutical compositions containing any of the inventive TCR materials can comprise more than one inventive TCR material, e.g., a polypeptide and a nucleic acid, or two or more different TCRs. Alternatively, the pharmaceutical composition can comprise an inventive TCR material in combination with another pharmaceutically active agents or drugs, such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used and is limited only by chemico-physical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. The following formulations for oral, aerosol, parenteral, subcutaneous, intravenous, intramuscular, intraarterial, intrathecal, and interperitoneal administration are exemplary and are in no way limiting. More than one route can be used to administer the inventive TCR materials, and in certain instances, a particular route can provide a more immediate and more effective response than another route.

Topical formulations are well-known to those of skill in the art. Such formulations are particularly suitable in the context of the invention for application to the skin.

Formulations suitable for oral administration can consist of (a) liquid solutions, such as an effective amount of the inventive TCR material dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and other pharmacologically compatible excipients. Lozenge forms can comprise the inventive TCR material in a flavor, usually sucrose and acacia or tragacanth, as well as pastilles comprising the inventive TCR material in an inert base, such as gelatin and glycerin, or sucrose and acacia, emulsions, gels, and the like containing, in addition to, such excipients as are known in the art.

The inventive TCR material, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The inventive TCR material can be administered in a physiologically acceptable diluent in a pharmaceutical carrier, such as a sterile liquid or mixture of liquids, including water, saline, aqueous dextrose and related sugar solutions, an alcohol, such as ethanol or hexadecyl alcohol, a glycol, such as propylene glycol or polyethylene glycol, dimethylsulfoxide, glycerol, ketals such as 2,2-dimethyl-1, 3-dioxolane-4-methanol, ethers, poly(ethyleneglycol) 400, oils, fatty acids, fatty acid esters or glycerides, or acetylated fatty acid glycerides with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-β-aminopropionates, and 2-alkyl-imidazoline quaternary ammonium salts, and (e) mixtures thereof.

The parenteral formulations will typically contain from about 0.5% to about 25%, or more, by weight of the inventive TCR material in solution. Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene glycol sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Injectable formulations are in accordance with the invention. The requirements for effective pharmaceutical carriers for injectable compositions are well-known to those of ordinary skill in the art (see, e.g., *Pharmaceutics and Pharmacy Practice*, J.B. Lippincott Company, Philadelphia, Pa., Banker and Chalmers, eds., pages 238-250 (1982), and *ASHP Handbook on Injectable Drugs*, Toissel, 4th ed., pages 622-630 (1986)). Preferably, when administering cells, e.g., T cells, the cells are administered via injection.

It will be appreciated by one of skill in the art that, in addition to the above-described pharmaceutical compositions, the inventive TCR materials of the invention can be formulated as inclusion complexes, such as cyclodextrin inclusion complexes, or liposomes.

For purposes of the invention, the amount or dose of the inventive TCR material administered should be sufficient to effect, e.g., a therapeutic or prophylactic response, in the subject or animal over a reasonable time frame. For example, the dose of the inventive TCR material should be sufficient to bind to a cancer antigen, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR, polypeptide, or protein upon administration of a given dose of such T cells to a mammal among a set of mammals of which is each given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the condition being treated. By way of example and not intending to limit the invention, the dose of the inventive TCR material can be about 0.001 to about 1000 mg/kg body weight of the subject being treated/day or more, from about 0.01 to about 10 mg/kg body weight/day or more, or about 0.01 mg to about 1 mg/kg body weight/day or more. In an embodiment in which the inventive TCR material is a population of cells, the number of cells administered may vary, e.g., from about $1\times10^6$ to about $1\times10^{11}$ cells or more.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a bridge to a targeting moiety. The practice of conjugating compounds, e.g., inventive TCR materials, to targeting moieties is known in the art. See, for instance, Wadwa et al., *J. Drug Targeting* 3: 111 (1995) and U.S. Pat. No. 5,087,616. The term "targeting moiety" as used herein, refers to any molecule or agent that specifically recognizes and binds to a cell-surface receptor, such that the targeting moiety directs the delivery of the inventive TCR materials to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T-cell receptor (TCR), B-cell receptor (BCR), CD28, Platelet-derived Growth Factor Receptor (PDGF), nicotinic acetylcholine receptor (nAChR), etc.). The term "bridge" as used herein, refers to any agent or molecule that links the inventive TCR materials to the targeting moiety. One of ordinary skill in the art recognizes that sites on the inventive TCR materials, which are not necessary for the function of the inventive TCR materials, are ideal sites for attaching a bridge and/or a targeting moiety, provided that the bridge and/or targeting moiety, once attached to the inventive TCR materials, do(es) not interfere with the function of the inventive TCR materials, i.e., the ability to bind to MAGE-A3 or MAGE-A12; or to detect, treat, or prevent cancer.

Alternatively, the inventive TCR materials can be modified into a depot form, such that the manner in which the inventive TCR materials is released into the body to which it is administered is controlled with respect to time and location within the body (see, for example, U.S. Pat. No. 4,450,150). Depot forms of inventive TCR materials can be, for example, an implantable composition comprising the inventive TCR materials and a porous or non-porous material, such as a polymer, wherein the inventive TCR materials is encapsulated by or diffused throughout the material and/or degradation of the non-porous material. The depot is then implanted into the desired location within the body and the inventive TCR materials are released from the implant at a predetermined rate.

It is contemplated that the inventive phaiinaceutical compositions, TCRs, polypeptides, proteins, nucleic acids, recombinant expression vectors, host cells, or populations of cells can be used in methods of treating or preventing cancer. Without being bound to a particular theory, the inventive TCRs are believed to bind specifically to MAGE-A3 MAGE-A12, such that the TCR (or related inventive polypeptide or protein) when expressed by a cell is able to mediate an immune response against a target cell expressing MAGE-A3 or MAGE-A12. In this regard, the invention provides a method of treating or preventing cancer in a host, comprising administering to the host any of the pharmaceutical compostions, TCRs, polypeptides, or proteins described herein, any nucleic acid or recombinant expression vector comprising a nucleotide sequence encoding any of the TCRs, polypeptides, proteins described herein, or any host cell or population of cells comprising a recombinant vector which encodes any of the TCRs, polypeptides, or proteins described herein, in an amount effective to treat or prevent cancer in the host.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of cancer in a host. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

Also provided is a method of detecting the presence of cancer in a host. The method comprises (i) contacting a sample comprising cells of the cancer with any of the inventive TCRs, polypeptides, proteins, nucleic acids, recombinant expression vectors, host cells, populations of cells, or antibodies, or antigen binding portions thereof, described herein, thereby foiining a complex, and detecting the complex, wherein detection of the complex is indicative of the presence of cancer in the host.

With respect to the inventive method of detecting cancer in a host, the sample of cells of the cancer can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the host. Preferably, the contacting is in vitro.

Also, detection of the complex can occur through any number of ways known in the art. For instance, the inventive TCRs, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the host. Preferably, the cells are autologous to the host.

With respect to the inventive methods, the cancer can be any cancer, including any of sarcomas (e.g., synovial sarcoma, osteogenic sarcoma, leiomyosarcoma uteri, and alveolar rhabdomyosarcoma), lymphomas (e.g., Hodgkin lymphoma and non-Hodgkin lymphoma), hepatocellular carcinoma, glioma, head cancers (e.g., squamous cell carcinoma), neck cancers (e.g., squamous cell carcinoma), acute lymphocytic cancer, leukemias (e.g., acute myeloid leukemia and chronic lymphocytic leukemia), bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic myeloid cancer, colon cancers (e.g., colon carcinoma), esophageal cancer, cervical cancer, gastric cancer, gastrointestinal carcinoid tumor, hypopharynx cancer, larynx cancer, liver cancers (e.g., hepatocellular carcinoma), lung cancers (e.g., non-small cell lung carcinoma), malignant mesothelioma, melanoma, multiple myeloma, nasopharynx cancer, ovarian cancer, pancreatic cancer, peritoneum, omentum, and mesentery cancer, pharynx cancer, prostate cancer, rectal cancer, kidney cancers (e.g., renal cell carcinoma), small intestine cancer, soft tissue cancer, stomach cancer, testicular cancer, thyroid cancer, and urothelial cancers (e.g., ureter cancer and urinary bladder cancer).

The host referred to in the inventive methods can be any host. Preferably, the host is a mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

EXAMPLE 1

This example demonstrates the cloning of TCR genes from T cell clones and the generation of TCR constructs.

Four T cell clones were initially identified that recognized epitopes of the MAGE-A gene family in the context of the dominant class I alleles HLA-A*01 and C*07. Approximately 30% of the melanoma patient population expresses HLA-A*01, and more than 95% of HLA-A*01+ individuals express the HLA-A*0101 sub-type, while more than 50% of melanoma patients express one of the two dominant HLA-C*07 sub-types, C*07:01 and C*07:02.

The expressed TCR α and β chains were isolated from two clones, A10 and 13-18, that recognized residues 168-176 of protein MAGE-A3 (MAGE-A3:168-176) in the context of HLA-A*01. In addition, HLA-C*07 restricted TCRs recognizing a peptide corresponding to residues 170-178 of the MAGE-A12 protein (MAGE-A12:170-178) were isolated from clones 502 and FM8.

The α and β chains encoding functional TCRs were isolated from two MAGE-A12 reactive, HLA-C*07 reactive T cell clones, PHIN LB831-501D/19, referred to "502" (Heidecker et al., *J. Immunol.*, 164: 6041-6045 (2000)) and "FM8" (Panelli et al., *J. Immunol.*, 164: 4382-4392 (2000)), as well as two MAGE-A3 reactive, HLA-A*01 restricted T cell clones, LAU147 CTL1 or 810/A10, referred to "A10" (Parmentier et al., *Nat. Immunol.*, 11: 449-454 (2010)) and NW1000 AVP-1 13-18, referred to "13-18." Briefly, oligo-dT was used to reverse transcribe total RNA isolated from the T cell clones into cDNA using the SMART RACE cDNA amplification kit (Clontech, Mountain View, Calif.). The TCR α and β chains expressed by the T cell clones were identified by carrying out 5'-RACE reactions using a primer 5'-CACTGTTGCTCTTGAA GTCC-3' (SEQ ID NO: 55) that is complementary to the TCR α chain constant region and 5'-CAGGCAGTAT CTGGAGTCATTGAG-3' (SEQ ID NO: 56) that is complementary to the TCR β chain constant region in combination with adaptor primers from the SMART RNA synthesis kit. After sequencing of the 5'-RACE products, full length gene products were amplified using specific primers designed to amplify the appropriate full length TCR α and β chains. The A10 TCR expresses AV12-1/BV24-1, 13-18 expresses AV12-3/BV15, 502 TCR expresses AV13-1/BV25-1, and FM8 expresses AV38-2/BV4-3.

Transcripts encoding the paired α and β chains for each of the four T cell clones were inserted into the MSGV1 retroviral expression vectors.

EXAMPLE 2

This example demonstrates the reactivity of cells expressing anti-MAGE-A3 TCR-A10 (SEQ ID NOs: 13 and 14) and anti-MAGE-A3 TCR 13-18 (SEQ ID NOs: 24 and 25) in response to HLA-A1+/MAGE-A3+ cells.

Anti-CD3 stimulated T cells transduced with TCR-A10 (SEQ ID NO: 46) and TCR 13-18 (SEQ ID NO: 48) were evaluated for their ability to recognize a panel of HLA-A*01+ melanoma cell lines that express MAGE-A3. Untransduced (UT) and transduced cells were co-cultured overnight with various tumor cell lines (Tables 1A, 1B and FIG. 6A), and interferon-gamma (IFN-γ) (pg/ml) was measured.

TABLE 1A

| Tumor | HLA-A*01 | Copies MAGE-A3 |
| --- | --- | --- |
| 1860 mel | + | 12,100 |
| 397 mel | + | 32,700 |
| SK23 mel | + | 18,400 |
| 2984 mel | + | 14,900 |
| 2951 mel | + | 12,300 |
| A375 mel | + | 3,670 |
| 537 mel | + | 4,270 |
| 1300-A1 mel | + | 7,280 |
| 1300 mel | − | 13,600 |
| 2661 RCC | + | <1,000 |

TABLE 1B

| Tumor | HLA-A*01 | MAGE-A3 |
| --- | --- | --- |
| 2984 mel | + | + |
| 397 mel | + | + |
| 2630 mel | + | + |
| 2556 mel | + | + |
| 526 mel | − | + |
| 624 mel | − | + |
| 2359 mel | − | + |
| 2661 RCC | + | − |

Figure 1A:
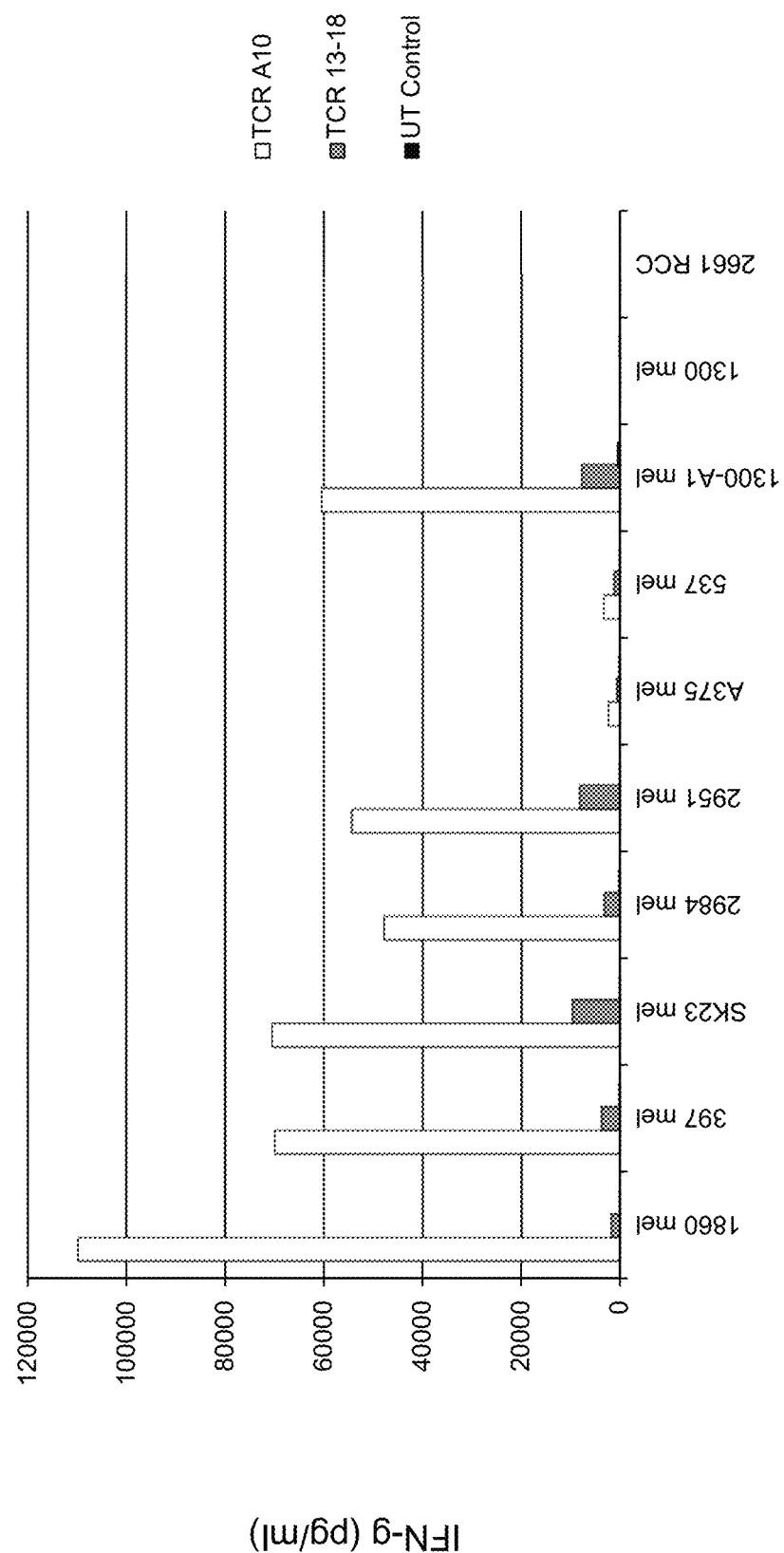

The results indicate that six of the eight HLA-A*01+/MAGE-A3+ melanoma cell lines that were evaluated stimulated higher levels of IFN-γ release from TCR A10 than from TCR 13-18-transduced T cells (FIG. 1A). Lower levels of IFN-γ were released following the co-culture of TCR-transduced T cells with two HLA-A1+ melanoma cell lines that expressed relatively low levels of MAGE-A3, A375 mel and 537 mel, but TCR A10-transduced T cells released higher levels of IFN-γ than TCR 13-18 transduced T cells in response to these target cells. These responses were restricted by HLA-A1 because 1300 mel, which lacked expression of HLA-A1, failed to stimulate IFN-γ release from TCR A10 and TCR 13-18-transduced cells, whereas a cell line generated by transfection of the parental 1300 mel cell line with HLA-A*01, designated 1300-A1, stimulated IFN-γ release from TCR A10 and TCR 13-18 transduced T cells. An HLA-A*01+ renal cancer cell line that lacked expression of MAGE-A3, 2661 RCC, failed to stimulate significant IFN-γ release from TCR A10 and TCR 13-18 transduced T cells. These results demonstrate that cells expressing TCR A10 release higher levels of IFN-γ than cells expressing TCR-13-18 when co-cultured with MAGE-A3+/HLA-A1+ target cells. These results also demonstrate that TCR A10 and TCR-13-18 are stimulated in the presence of MAGE-A3+/HLA-A1+ target cells.

The results of co-culture assays carried out with transduced PBMC demonstrated that TCR A10-transduced T cells generated high levels of IFN-gamma in response to the HLA-A*01+/MAGE-A3+ tumor cell lines 397 mel, 2984 mel, and 2556 mel. The cytokine levels were between five and ten times those generated from TCR 13-18 transduced T cells (FIG. 6A). The MAGE-A3+ but HLA-A*01 negative cell lines 562, 624 and 2359 mel, as well as the MAGE-A3 negative but HLA-A*01+ renal cancer cell line 2661 RCC failed to stimulate significant levels of cytokine from either TCR A10 or 13-18 transduced T cells (FIG. 6A).

The levels of transduction of the TCRs were evaluated using a quantitative PCR assay carried out using genomic DNA with forward (SEQ ID NO: 58) and reverse (SEQ ID NO: 59) primers and a probe (SEQ ID NO: 60) designed to specifically detect the MSGV1 retroviral LTR but not human endogenous retroviral sequences. Levels of the amplified products were nonnalized to a positive control sample of PBMC that had been transduced with a TCR directed against the NY-ESO-1:157-165 epitope that was estimated to contain approximately 80% transduced T cells by staining with an NY-ESO-1 tetramer.

The differences in activity of T cells transduced with the A10 or 13-18 TCR did not appear to be due to differences in the frequency of transduction with the two TCRs, as they appeared to be equivalent (FIG. 6B). In addition, T cells transduced with the A10 TCR recognized target cells incubated with a minimum concentration of 0.5 nM MAGE-A3 168-176 peptide, which was a 10-fold lower concentration than required for recognition by cells transduced with the 13-18 TCR (FIG. 6C), indicating that the A10 TCR possessed a higher functional avidity than the 13-18 TCR.

The ability of fresh, un-cultured tumor cells to stimulate T cells transduced with either TCR A10 (SEQ ID NO: 46) or DMF5 (a TCR directed against the HLA-A*0201/MART-1:27-35 T cell epitope), was evaluated. Untransduced (UT) and transduced cells were co-cultured with various fresh tumors, and IFN-γ (pg/ml) was measured.

Figure 1B:
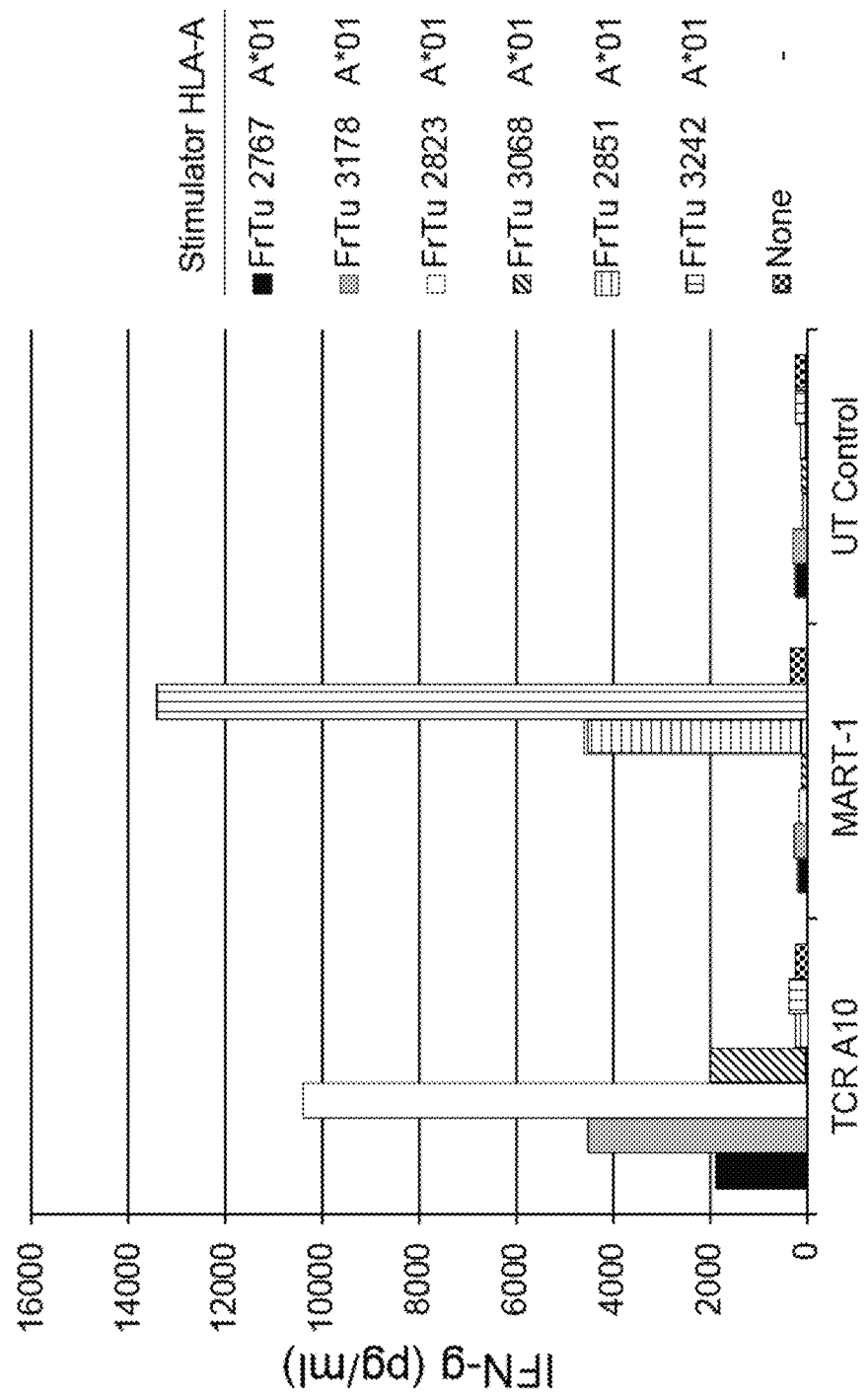

The results indicated that TCR A10 transduced T cells recognized four of the four HLA-A*01+/MAGE-A3+ fresh tumors that were tested (FrTu 2767, FrTu 3178, FrTu 2823 and FrTu 3068), and DMF5-transduced T cells recognized both of the HLA-A*0201+/MART-1+ fresh tumor cells that were tested (FrTu 2851 and FrTu 3242) (FIG. 1B). The TCR A10 transduced T cells failed to recognize HLA-A*0201+ fresh tumors, while DMF5 transduced T cells failed to recognize HLA-A*01+ fresh tumors, indicating that the IFN-γ secretion by TCR A10 was a HLA-A1+/MAGE-A3+-specific response.

T cells that were transduced with TCR A10 and 13-18 recognized five of six MAGE-A3+ and HLA-A*01+ fresh tumors (FrTu), FrTu 3178, 2767, 2823, 2830 and 3068, but did not recognize either FrTu 2685, an HLA-A*01+ fresh tumor that lacked expression of MAGE-A3 or the three MAGE-A3+ fresh tumors, FrTu 2181, 3242 and 2803, that lacked expression of HLA-A*01 (FIG. 7A; Table 1C).

TABLE 1C

| Fresh Tumor | HLA-A*01 | MAGE-A3 |
|---|---|---|
| 3178 | + | + |
| 2767 | + | + |
| 2823 | + | + |
| 2830 | + | + |
| 3068 | + | + |
| 2268 | + | + |
| 2685 | + | − |
| 2181 | − | + |
| 3242 | − | + |
| 2803 | − | + |

EXAMPLE 3

This example demonstrates the reactivity of cells expressing anti-MAGE-A12 TCR 502 (SEQ ID NOs: 34 and 35) or anti-MAGE-A12 TCR FM8 (SEQ ID NOs: 44 and 45) in response to co-culture with HLA-Cw*07+/MAGE-A12+ cells.

Anti-CD3 stimulated CD8+ T cells isolated from two patient PBMC samples were transduced with a control construct encoding the truncated human low affinity nerve growth factor receptor (NGFR), TCR 502 (SEQ ID NO: 47), or TCR FM8 (SEQ ID NO: 49) were evaluated for their ability to recognize a panel of Cw*07+ melanoma cell lines that express MAGE-A12.

Expression of the MAGE-A12 gene product was evaluated by Q-PCR using two primers (SEQ ID NOs: 61 and 62) designed to specifically amplify the MAGE-A12 gene product but not other members of the MAGE-A gene family as well as a MAGE-A12 specific probe (SEQ ID NO: 63). Antigen expression was determined using plasmid controls as standards for estimating copy numbers and using glyceraldehyde 3-phosphate dehydrogenase (GAPDH) for normalization. Tumor cell lines and fresh tumors expressing greater than 1,000 copies of MAGE-A12 per 106 copies of GAPDH were denoted as positive for MAGE-A12 expression.

Transduced cells were co-cultured overnight with various tumor cell lines (Table 2A; FIGS. 6D and 6F), and IFN-γ (pg/ml) was measured.

TABLE 2A

| Stimulator | HLA-C allele | MAGE-A12 |
|---|---|---|
| 1910 mel | 0701, 0303 | + |
| 586 mel | 0701 | + |
| 2359 mel | 0701, 16 | + |
| F002 mel | 0701, 1203 | + |
| 1300 mel | 0702 | + |
| 624 mel | 0702, 0802 | + |
| SK23 mel | 0701, 0702 | + |
| 1909 mel | 0701, 0702 | + |
| 1011 mel | 0702 | − |
| 397 mel | 0701 | + |
| 526 mel | — | + |
| 2556 mel | — | + |
| 2984 mel | — | + |
| 2630 mel | 0701 | − |

Figure 2A:
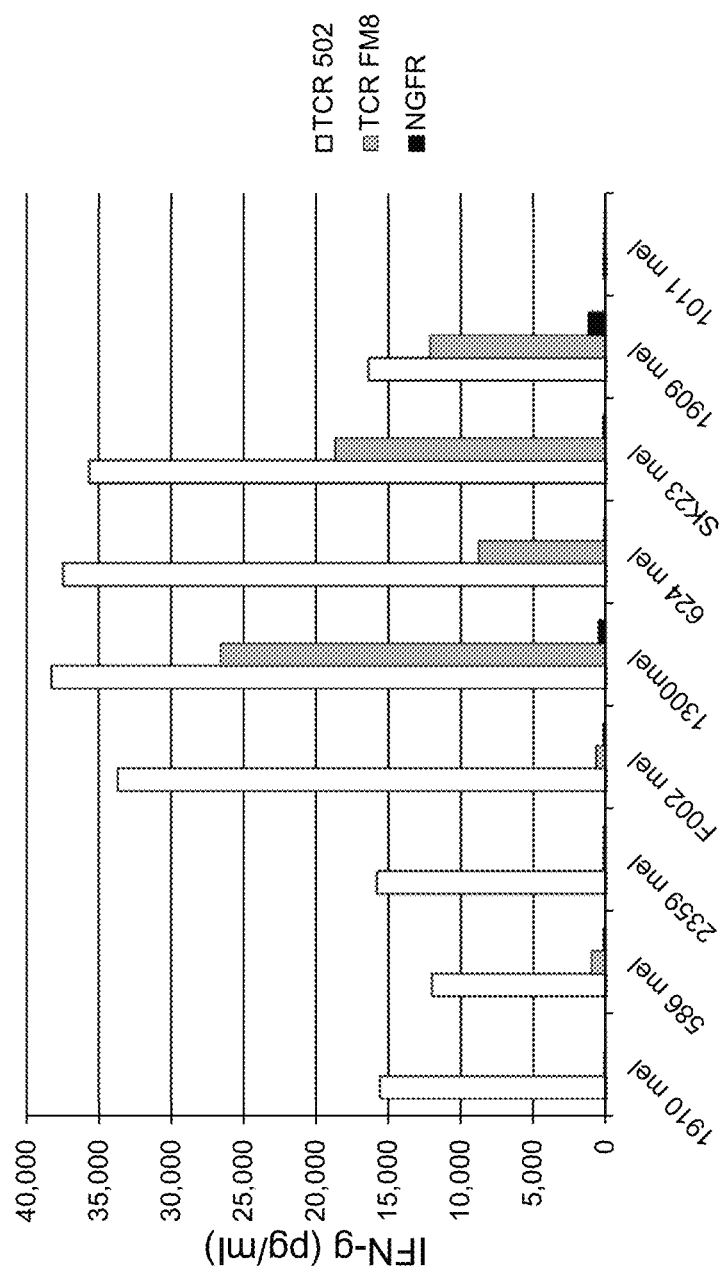
Figure 2B:
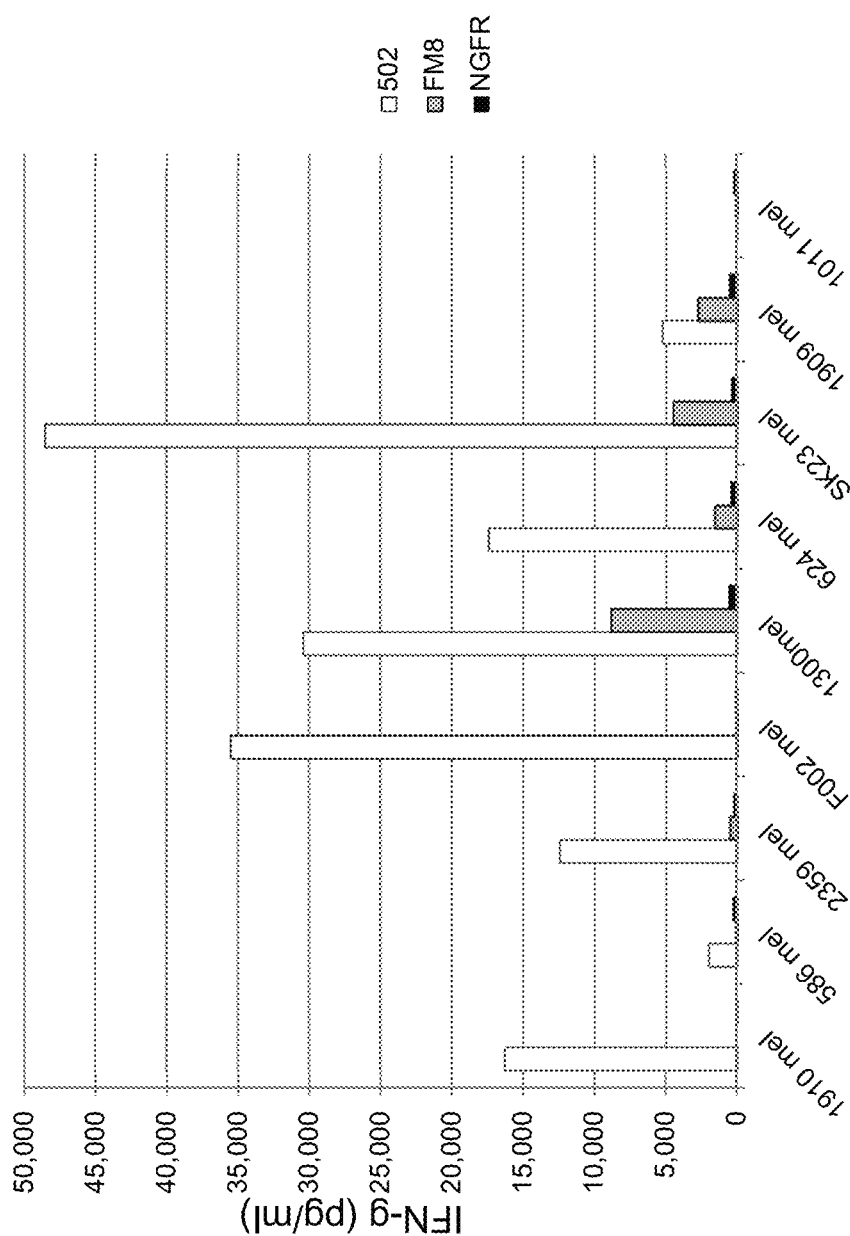

The results demonstrated that T-cells transduced with TCR 502 recognized eight of the eight MAGE-A12+ melanoma cell lines tested that express either HLA-Cw*0701 or 0702, whereas T cells transduced with TCR FM8 only recognized melanoma cell lines that express HLA-Cw*0702 (FIGS. 2A and 2B; see also FIG. 6F). In addition, TCR 502 transduced T cells released higher levels of IFN-γ in response to the HLA-Cw*0702+ targets SK23 mel, 1300 mel and 624 mel as compared to TCR FM8 transduced T cells (FIGS. 6D and 6F). The 1011 mel cells, which expressed HLA-Cw*0702 but lacked expression of MAGE-A12, did not stimulate significant cytokine release from cells transduced with TCR 502 or TCR FM8. T cells transduced with a control construct encoding NGFR failed to respond significantly to any of the targets tested. These results demonstrate that cells expressing TCR 502 release higher levels of IFN-γ than cells expressing TCR FM8 when co-cultured with MAGE-A12+/HLA-Cw7 target cells and that TCR 502 recognizes MAGE-A12 in the context of either HLA-Cw0701 or HLA-Cw0702. These results also demonstrate that TCR A502 and TCR FM8 are stimulated in the presence of MAGE-A12+ cells.

Figure 6E:
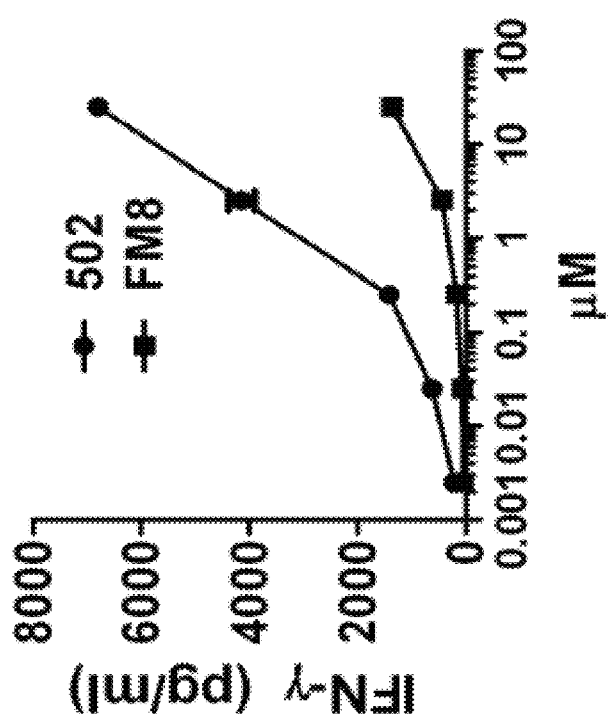

The TCR 502 transduced T cells recognized the HLA-C*0702+, MAGE-A12+ tumor 624 mel as well as two HLA-C*07:01+, MAGE-A12+ tumors, 397 and 2359 mel, whereas FM8 transduced T cells recognized the HLA-C*07:02+ tumor cell line 624 mel but failed to recognize 397 and 2359 mel (FIG. 6D). Neither population of transduced T cells recognized 526, 2556, or 2984 mel, MAGE-A3+ melanoma cell lines that lacked expression of HLA-C*07, or 2630 mel, an HLA-C*07:01+ tumor cell line that lacked expression of MAGE-A12 (FIG. 6D). These differences did not appear to be due to differences in transduction frequencies of the two TCRs (measured as described in Example 2), which appeared to be similar in cells transduced with either TCR (FIG. 6B). In addition, cells transduced with the 502 TCR recognized target cells incubated with a minimum concentration of 2.5 nM MAGE-A12:170-178, a 100-fold lower concentration than that required for recognition by cells transduced with the FM8 TCR (FIG. 6E), indicating that the 502 TCR possessed a higher functional avidity than the FM8 TCR.

The T cells that were transduced with MAGE-A12 reactive TCRs were then evaluated for their responses to enzymatic digests of fresh, un-cultured tumor cells. The T cells transduced with TCR 502 recognized one of the four MAGE-A12+ fresh tumors that expressed HLA-C*0701, FrTu 3068, and TCR 502 as well as FM8 transduced T cells recognized one of the two MAGE-A12+ tumors that expressed HLA-C*07:02, FrTu 2181 (FIG. 7B; Table 2B). Neither population of TCR transduced T cells recognized the HLA-C*07:01⁻ and 07:02⁻ fresh tumors 2767 or 2823, or the MAGE-A12⁻ tumors 2685, 3242 and 2803 that lacked expression of MAGE-A12.

TABLE 2B

| Fresh Tumor | HLA-C*07 | MAGE-A12 |
|---|---|---|
| 3068 | 01 | + |
| 2181 | 02 | + |
| 3178 | 01 | + |
| 2830 | 01 | + |
| 2268 | 01, 02 | + |
| 2767 | — | + |
| 2823 | — | + |
| 2685 | 01 | − |
| 3242 | 01 | − |
| 2803 | 02 | − |

EXAMPLE 4

This example demonstrates the population that may be treated using the inventive TCRs.

Approximately 28% of the patient population expresses HLA-A*01, and approximately 54% of the patient population expresses HLA-Cw*07. Two dominant subtypes of HLA-Cw*07, Cw*0701 and Cw*0702, are expressed by approximately 27% and approximately 31% of the patient population, respectively. FIG. 3A illustrates the cumulative percentage of the population that would be expected to be treatable by the use of TCRs restricted by HLA-A1, HLA-A2, and/or HLA-Cw7 (based upon the percentages of these alleles in the nomial Caucasian population).

Because approximately 30% of patients express high levels of MAGE-A3 and MAGE-A12, the use of the inventive TCRs will allow a significantly higher percentage of patients to be eligible for TCR-based adoptive immunotherapies. FIGS. 3B and 3C illustrate the cumulative percentage of the human melanoma (FIG. 3B) and synovial cell sarcoma (FIG. 3C) patient populations that would be expected to be treatable using TCRs that recognize NY-ESO-1 in the context of HLA-A2; MAGE-A3 in the context of HLA-A1; MAGE-A3 and MAGE-A12 in the context of HLA-A2; and/or MAGE-A12 in the context of HLA-Cw7.

EXAMPLE 5

This example demonstrates the reactivity of cells expressing TCR 502 or TCR FM8 in response to co-culture with HLA-Cw*0701 or HLA-Cw*0702-expressing target cells pulsed with peptides of various proteins from the MAGE family.

Cells transduced with NGFR, TCR 502 (SEQ ID NO: 47), or TCR FM8 (SEQ ID NO: 49) were co-cultured with cells expressing HLA-Cw*0701 or HLA-Cw*0702. IFN-γ (pg/ml) secretion was measured.

Figure 4:
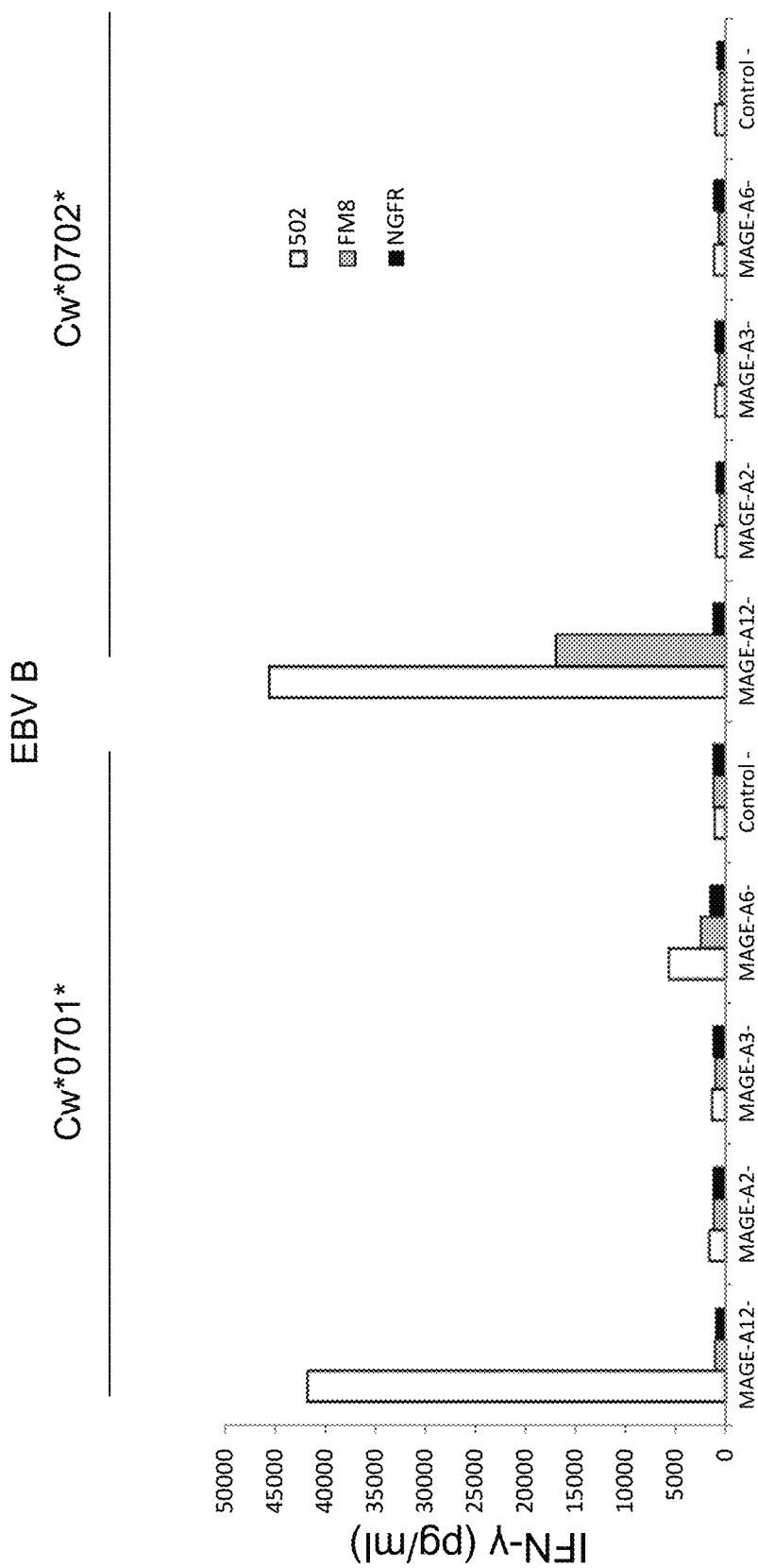
Figures 5A, 5B:
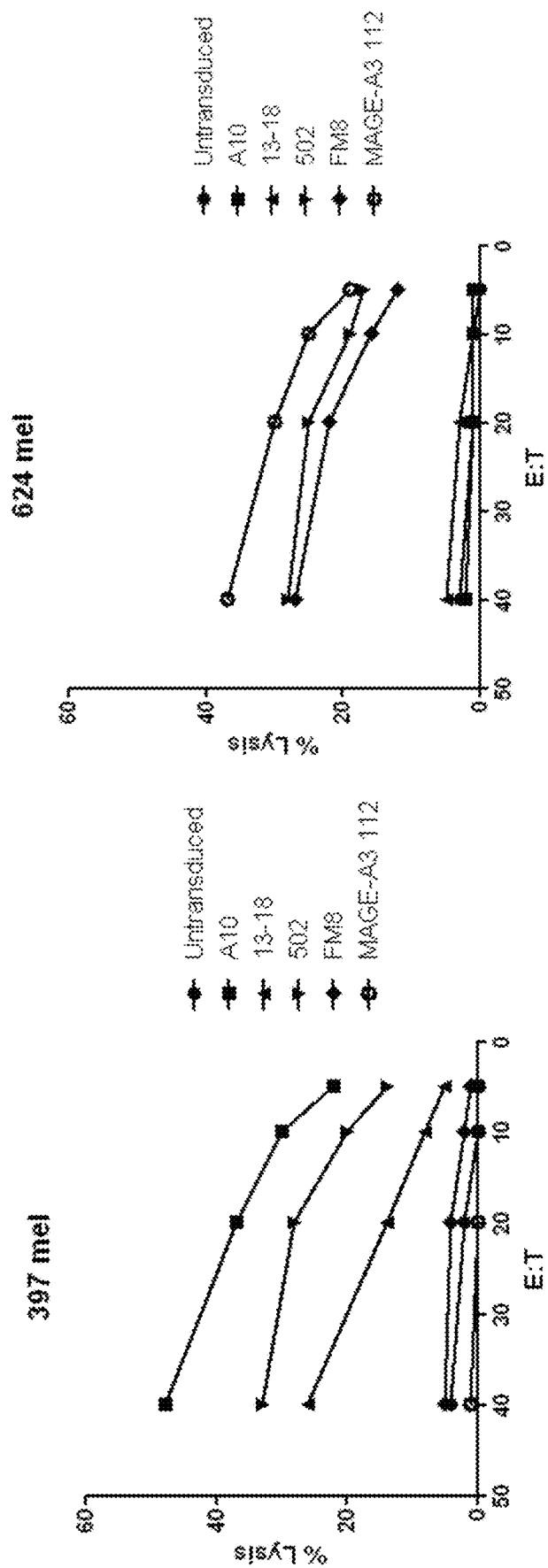
Figure 5D:
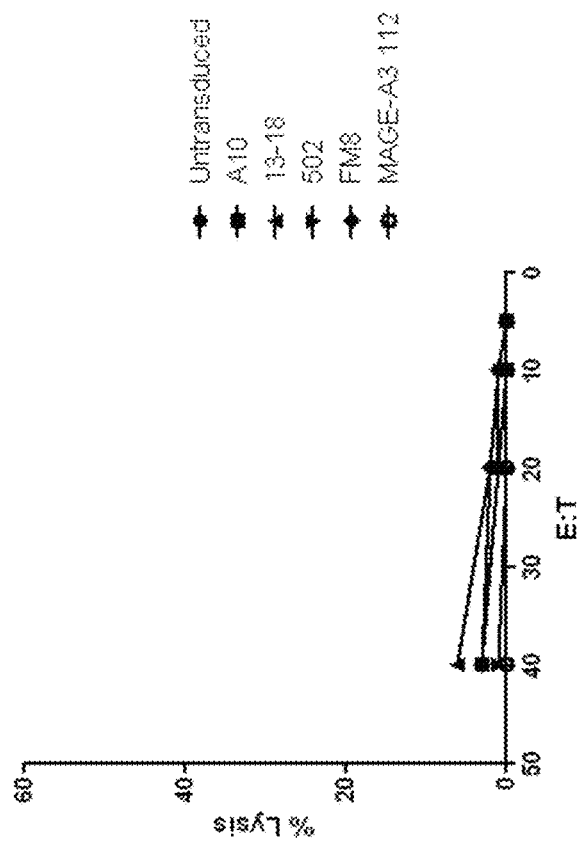
Figure 5C:
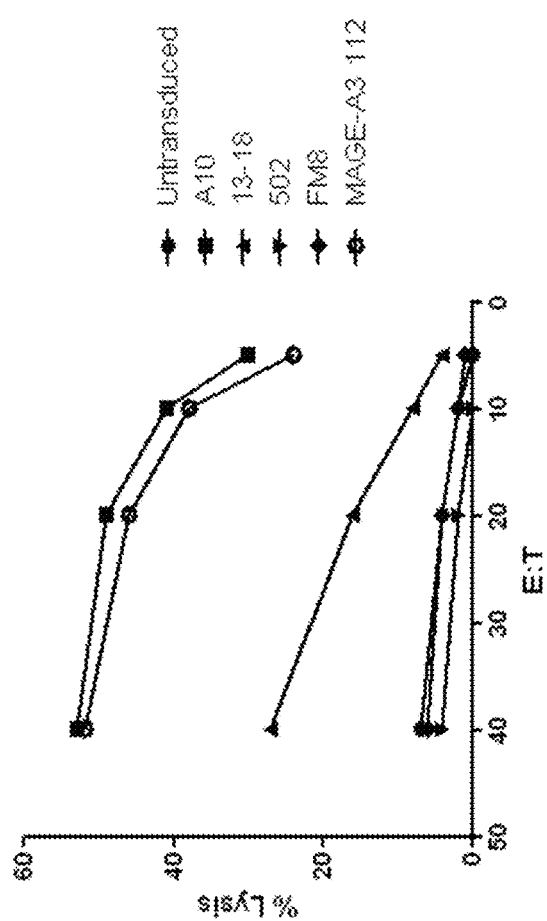

The results demonstrated that cells transduced with TCR 502 recognize cells expressing HLA-Cw*0701 or HLA-Cw*0702 when pulsed with MAGE-A12 (VRIGHLYIL; SEQ ID NO: 4), and that cells transduced with TCR FM8 recognized cells expressing HLA-Cw*0702 when pulsed with MAGE-A12 (VRIGHLYIL; SEQ ID NO: 4) (FIG. 4). Cells transduced with NGFR showed no significant reactivity.

EXAMPLE 6

This example demonstrates the specificity of the anti-MAGE-A3 and anti-MAGE-A12 TCRs.

Following stimulation with anti-CD3 antibody, PMBC from a single donor were transduced with PBMC that were untransduced or transduced with anti-MAGE-A12 TCR 502 (SEQ ID NO: 47), anti-MAGE-A12 TCR FM8 (SEQ ID NO: 49), anti-MAGE-A3 TCR A10 (SEQ ID NO: 46), anti-MAGE-A3 TCR 13-18 (SEQ ID NO: 48), or anti-MAGE-A3 TCR 112-120. Thirteen days after stimulation, transduced T cells were incubated with the tumor targets set forth in Table 3 in a standard 4 hour $^{51}$Cr release assay.

TABLE 3

|  | MAGE-A3 | MAGE-A12 | HLA-A | HLA-C |
|---|---|---|---|---|
| 397 mel | + | + | 01/02 | 0401/0701 |
| 624 mel | + | + | 02/03 | 0702/0802 |
| 2984 mel | + | + | 01/02 | 06 |
| 2661 RCC | − | − | 01/02 | 07 |

As shown in FIGS. 5(A)-5(D), anti-MAGE-A12 TCR 502 specifically lysed tumor cells that expressed MAGE-A12 and HLA-Cw7 and did not lyse tumor cells that lacked expression of MAGE-A12 or HLA-Cw7. Anti-MAGE-A3 TCR A10 specifically lysed tumor cells that expressed MAGE-A3 and HLA-A1 and did not lyse tumor cells that lacked expression of MAGE-A3 or HLA-A1.

EXAMPLE 7

This example demonstrates the specificity of the anti-MAGE-A3 and anti-MAGE-A12 TCRs.

The monkey kidney cell line COS-7 was transiently transfected with either HLA-A*01, C*07:01 or C*07:02 plus either MAGE-A3, A1, A2, A4, A6, A9, A10 or A12 overnight. The following day T cells transduced with either TCR A10, 13-18 or un-transduced control cells or TCR 502, FM8 or un-transduced control cells were added and the release of soluble IFN-gamma was evaluated following an overnight co-culture by ELISA.

T cells transduced with the MAGE-A3-reactive TCR A10 recognize HLA-A1$^+$ target cells transfected with MAGE-A3 but failed to recognize targets transfected with MAGE-A1, A2, A4, A6, A9, A10 or A12 constructs (FIG. 8A) that encoded peptides that differed at between one and three positions from the MAGE-A3:170-178 epitope. The T cells that were transduced with either TCR 502 or FM8 recognized HLA-C*07:02$^+$ targets transfected with MAGE-A12 but not MAGE-A3, A1, A2, A4,A6, A9, A10 (FIG. 8B), while T cells transduced with TCR 502 but not FM8 recognized HLA-C*07:01$^+$ targets transfected with MAGE-A12 but not the additional MAGE-A family members tested (FIG. 8C).

EXAMPLE 8

This example demonstrates the reactivity of transduced T cells.

Purified CD8+ and CD4+ T cells were isolated by negative selection using CD8 and CD4 T lymphocyte enrichment kits (Becton/Dickinson, Franklin Lakes, N.J.), followed by positive selection using CD8 and CD4 magnetic beads (Becton/Dickinson). The isolated CD8+ and CD4+ cells were estimated by fluorescence activated cell sorting (FACS) analysis to contain less than 1% contaminating CD4+ and CD8+ T cells, respectively.

The responses of separated populations of CD8+ and CD4+ T cells transduced with TCRs to tumor cell targets was then evaluated. Highly purified CD4+ T cells transduced with TCR A10 containing fewer than 1% contaminating CD8+ T cells released low but significant levels of IFN-gamma in response to MAGE-A3+ tumor cell line 397 mel as well as the MAGE-A3+ tumor cell line 1300A1 mel that was stably transfected with HLA-A*01 (Table 4A; FIG. 9B). CD8+ T cells transduced with TCR A10 released interferon-gamma in response to 397 mel or 1300-A1 mel (Table 4A; FIG. 9A). CD8+ T cells transduced with TCR 502 or TCR FM8 released interferon-gamma in response to 624 mel, and TCR 502 released interferon-gamma in response to 397 mel (FIG. 9C and Table 4B).

TABLE 4A

| Cell Line | HLA-A*01 | MAGE-A3 |
|---|---|---|
| 397 mel | + | + |
| 1300 mel | + | + |

TABLE 4A-continued

| Cell Line | HLA-A*01 | MAGE-A3 |
|---|---|---|
| 1300-A1 mel | + | + |
| 624 mel | − | + |
| 2359 mel | − | + |
| 2661 RCC | + | − |

TABLE 4B

| Cell Line | HLA-C*07 | MAGE-A12 |
|---|---|---|
| 397 mel | 01 | + |
| 624 mel | 02 | + |
| 2359 mel | 01 | + |
| 526 mel | − | + |
| 2661 RCC | − | − |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An isolated or purified nucleic acid comprising a nucleotide sequence encoding a T cell receptor (TCR) having antigenic specificity for MAGE-A12 presented by HLA-Cw7, wherein the TCR comprises the amino acid sequences of SEQ ID NOs: 26-31.

2. The isolated or purified nucleic acid of claim 1, wherein the TCR has antigenic specificity for a MAGE-A12 epitope comprising VRIGHLYIL (SEQ ID NO: 4).

3. The isolated or purified nucleic acid of claim 1, wherein the TCR comprises the amino acid sequences of SEQ ID NOs: 32-33.

4. The isolated or purified nucleic acid of claim 3, wherein the TCR comprises the amino acid sequences of SEQ ID NOs: 34-35.

5. An isolated or purified nucleic acid comprising a nucleotide sequence encoding a polypeptide, wherein the polypeptide comprises the amino acid sequences of SEQ ID NOs: 26-31.

6. The isolated or purified nucleic acid of claim 5, wherein the polypeptide comprises the amino acid sequences of SEQ ID NOs: 32-33.

7. The isolated or purified nucleic acid of claim 6, wherein the polypeptide comprises the amino acid sequences of SEQ ID NOs: 34-35.

8. An isolated or purified nucleic acid comprising a nucleotide sequence encoding a protein, wherein the protein comprises:
a first polypeptide chain comprising the amino acid sequences of SEQ ID NOs: 26-28; and
a second polypeptide chain comprising the amino acid sequences of SEQ ID NOs: 29-31.

9. The isolated or purified nucleic acid of claim 8, wherein the protein comprises:
a first polypeptide chain comprising the amino acid sequence of SEQ ID NO: 32; and
a second polypeptide chain comprising the amino acid sequence of SEQ ID NO: 33.

10. The isolated or purified nucleic acid of claim 9, wherein the protein comprises:
a first polypeptide chain comprising the amino acid sequence of SEQ ID NO: 34; and
a second polypeptide chain comprising the amino acid sequence of SEQ ID NO: 35.

11. The isolated or purified nucleic acid of claim 8, wherein the protein is a fusion protein.

12. The isolated or purified nucleic acid of claim 8, wherein the protein is a recombinant antibody.

13. The isolated or purified nucleic acid of claim 1, comprising a nucleotide sequence comprising SEQ ID NO: 47.

14. An isolated or purified nucleic acid comprising a nucleotide sequence which is complementary to the nucleotide sequence of the nucleic acid of claim 1.

15. An isolated or purified nucleic acid comprising a nucleotide sequence which hybridizes under stringent conditions to the nucleotide sequence of the nucleic acid of claim 1.

16. A recombinant expression vector comprising the nucleic acid of claim 1.

17. An isolated host cell comprising the recombinant expression vector of claim 16.

18. The isolated host cell of claim 17, wherein the cell is a peripheral blood lymphocyte (PBL).

19. The isolated host cell of claim 18, wherein the PBL is a T cell.

20. The isolated host cell of claim 17, wherein the cell is a tumor infiltrating lymphocyte (TIL).

21. A population of cells comprising at least one host cell of claim 17.

22. A pharmaceutical composition comprising the population of cells of claim 21 and a pharmaceutically acceptable carrier.

23. A method of detecting the presence of cancer in a host, comprising:
(i) contacting a sample comprising cells of the cancer with the population of cells of claim 21, thereby forming a complex, and
(ii) detecting the complex,
wherein detection of the complex is indicative of the presence of cancer in the host and
wherein the cancer is melanoma or urinary bladder cancer and the cancer expresses a MAGE-A12 epitope comprising VRIGHLYIL (SEQ ID NO: 4) presented by HLA-Cw7.

24. A method of treating cancer in a host, comprising administering to the host the population of cells of claim 21, in an amount effective to treat cancer in the host, wherein the cancer is melanoma or urinary bladder cancer and the cancer expresses a MAGE-A12 epitope comprising VRIGHLYIL (SEQ ID NO: 4) presented by HLA-Cw7.

25. The method of claim 23, wherein the host cell is a cell that is autologous to the host.

26. The method of claim 23, wherein the cells of the population are cells that are autologous to the host.

* * * * *